(12) United States Patent
Hughes et al.

(10) Patent No.: US 11,293,028 B2
(45) Date of Patent: Apr. 5, 2022

(54) COMPOSITIONS FOR ADJUSTABLE RIBOSOME TRANSLATION SPEED AND METHODS OF USE

(71) Applicant: University of Utah Research Foundation, Salt Lake City, UT (US)

(72) Inventors: Kelly T. Hughes, Salt Lake City, UT (US); Fabienne Chevance, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 472 days.

(21) Appl. No.: 15/765,132

(22) PCT Filed: Oct. 3, 2016

(86) PCT No.: PCT/US2016/055162
§ 371 (c)(1),
(2) Date: Mar. 30, 2018

(87) PCT Pub. No.: WO2017/059424
PCT Pub. Date: Apr. 6, 2017

(65) Prior Publication Data
US 2018/0282738 A1 Oct. 4, 2018

Related U.S. Application Data

(60) Provisional application No. 62/263,404, filed on Dec. 4, 2015, provisional application No. 62/236,477, filed on Oct. 2, 2015.

(51) Int. Cl.
| | |
|---|---|
| *C12N 15/00* | (2006.01) |
| *C12N 15/74* | (2006.01) |
| *C07K 14/62* | (2006.01) |
| *C07K 14/245* | (2006.01) |

(52) U.S. Cl.
CPC ............ *C12N 15/74* (2013.01); *C07K 14/245* (2013.01); *C07K 14/62* (2013.01); *C07K 2319/00* (2013.01); *C07K 2319/21* (2013.01); *C07K 2319/50* (2013.01)

(58) Field of Classification Search
CPC ...... C12N 15/74; C07K 14/245; C07K 14/62; C07K 2319/21; C07K 2319/50; C07K 2319/00
See application file for complete search history.

(56) References Cited

U.S. PATENT DOCUMENTS

| | | | |
|---|---|---|---|
| 9,630,997 | B2 | 4/2017 | Hughes et al. |
| 10,800,818 | B2 | 10/2020 | Hughes et al. |
| 2005/0196865 | A1 | 9/2005 | Frazer |
| 2010/0290996 | A1 | 11/2010 | Nickerson et al. |
| 2012/0027786 | A1 | 2/2012 | Gupta et al. |
| 2013/0121915 | A1 | 5/2013 | Paas et al. |
| 2014/0244228 | A1 | 8/2014 | Lee et al. |
| 2015/0225466 | A1 | 8/2015 | Hughes et al. |
| 2018/0009851 | A1 | 1/2018 | Hughes et al. |

FOREIGN PATENT DOCUMENTS

| | | |
|---|---|---|
| JP | 2015523066 A | 8/2015 |
| WO | WO-2001/070955 A2 | 9/2001 |
| WO | WO-2013181404 A1 | 12/2013 |
| WO | WO-2017059424 A1 | 4/2017 |

OTHER PUBLICATIONS

Sinclair et al., Prot. Exp. Puf. 26:96-105 (Year: 2002).*
Angov et al., PLoS One, 3 (5) e2189 (Year: 2008).*
Abramoff, M.D., et al., "Image Processing with ImageJ," Biophotonics International 11(7):36-42, Laurin Publishing Co. Inc., United States (2004).
Aldridge, C., et al., "The Interaction Dynamics of a Negative Feedback Loop Regulates Flagellar Number in *Salmonella enterica* Serovar Typhimurium," Molecular Microbiology 78(6):1416-1430, Blackwell Scientific Publications, England (2010).
Aldridge, P.D., et al., "The Flagellar-specific Transcription Factor, $\sigma^{28}$, is the Type III Secretion Chaperone for the Flagellar-specific Anti-$\sigma^{28}$ Factor FlgM," Genes and Development 20(16):2315-2326, Cold Spring Harbor Laboratory Press, United States (2006).
Auvray, F., et al., "Flagellin Polymerisation Control by a Cytosolic Export Chaperone," Journal of Molecular Biology 308(2):221-229, Elsevier, England (2001).
Baneyx, F. and Georgiou, G., "In Vivo Degradation of Secreted Fusion Proteins by the *Escherichia coli* Outer Membrane Protease OmpT," Journal of Bacteriology 172(1):491-494, American Society for Microbiology, United States (1990).
Barembruch, C. and Hengge, R., "Cellular Levels and Activity of the Flagellar Sigma Factor FliA of *Escherichia coli* are Controlled by FlgM-modulated Proteolysis," Molecular Microbiology 65(1):76-89, Blackwell Scientific Publications, England (2007).
Berg, H.C. and Anderson, R.A., "Bacteria Swim by Rotating their Flagellar Filaments," Nature 245(5425):380-382, Nature Publishing Group, England (1973).
Bonifield, H.R. and Hughes, K.T., "Flagellar Phase Variation in *Salmonella enterica* Is Mediated by a Posttranscriptional Control Mechanism," Journal of Bacteriology 185(12):3567-3574, American Society for Microbiology, United States (2003).
Bulaj, G., et al., "Novel Conotoxins from *Conus striatus* and *Conus kinoshitai* Selectively Block TTX-resistant Sodium Channels," Biochemistry 44(19):7259-7265, American Chemical Society, United States (2005).
Chadsey, M.S. and Hughes, K.T., "A Multipartite Interaction Between *Salmonella* Transcription Factor $\sigma^{28}$ and its Anti-$\sigma$ Factor FlgM: Implications for $\sigma^{28}$ Holoenzyme Destabilization through Stepwise Binding," Journal of Molecular Biology 306(5):915-929, Elsevier, England (2001).

(Continued)

*Primary Examiner* — Catherine S Hibbert
(74) *Attorney, Agent, or Firm* — Sterne, Kessler, Goldstein & Fox P.L.L.C.

(57) ABSTRACT

The present invention relates to the effects of codon context and synonymous codon changes on mRNA translation and methods of increasing protein production.

Figure 1:
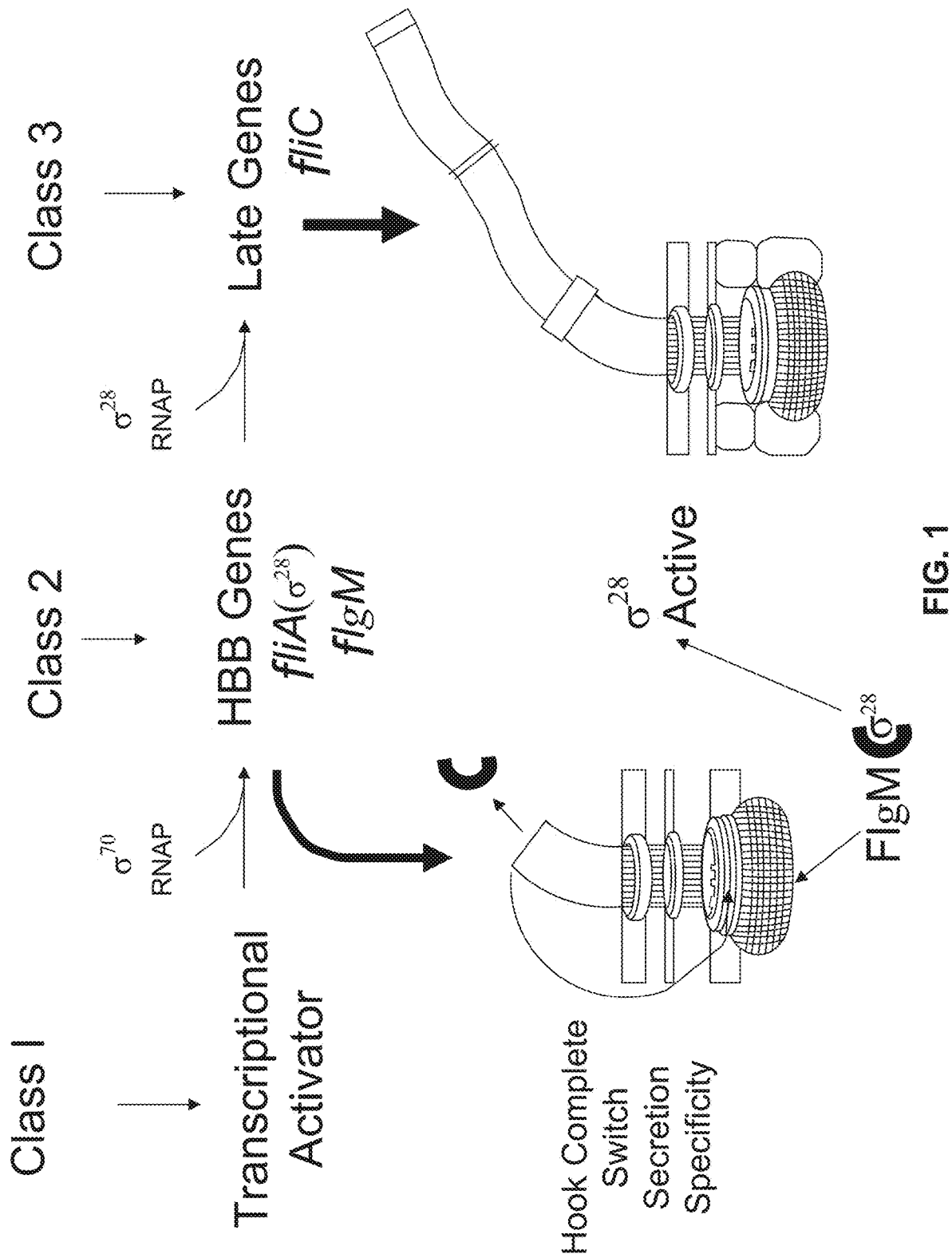

10 Claims, 4 Drawing Sheets
Specification includes a Sequence Listing.

(56) References Cited

OTHER PUBLICATIONS

Chadsey, M.S., et al., "The Flagellar Anti-σ Factor FlgM Actively Dissociates *Salmonella typhimurium* σ$^{28}$ RNA Polymerase Holoenzyme," Genes and Development 12(19):3123-3136, Cold Spring Harbor Laboratory Press, United States (1998).

Chahine, M., et al., "Characterizing the μ-conotoxin Binding Site on Voltage-sensitive Sodium Channels with Toxin Analogs and Channel Mutations," Receptors and Channels 3(3):161-174, Taylor and Francis, England (1995).

Chahine, M., et al., "Extrapore Residues of the S5-S6 Loop of Domain 2 of the Voltage-gated Skeletal Muscle Sodium Channel (rSkM1) Contribute to the μ-conotoxin GIIIA Binding Site," Biophysical Journal 75(1):236-246, Cell Press, United States (1998).

Chang, N.S., et al., "Predominant Interactions Between μ-conotoxin Arg-13 and the Skeletal Muscle Na$^+$ Channel Localized by Mutant Cycle Analysis," Biochemistry 37(13):4407-4419, American Chemical Society, United States (1998).

Che, N., et al., "Soluble Expression and One-step Purification of a Neurotoxin Huwentoxin-I in *Escherichia coli*," Protein Expression and Purification 65(12):154-159, Academic Press, United States (2009).

Chevance, F.F. and Hughes, K.T., "Coordinating Assembly of a Bacterial Macromolecular Machine," Nature Reviews. Microbiology 6(6):455-465, Nature Publishing Group, England (2008).

Chubiz, J.E., et al., "FliZ Regulates Expression of the *Salmonella* Pathogenicity Island 1 Invasion Locus by Controlling HilD Protein Activity in *Salmonella enterica* Serovar Typhimurium," Journal of Bacteriology 192(23):6261-6270, American Society for Microbiology, United States (2010).

Datsenko, K.A. and Wanner, B.L., "One-Step Inactivation of Chromosomal Genes in *Escherichia coli* K-12 Using PCR Products," Proceedings of the National Academy of Sciences of the United States of America 97(12):6640-6645, National Academy of Sciences, United States (2000).

Daughdrill, G.W., et al., "The C-terminal Half of the Anti-sigma Factor, FlgM, Becomes Structured When Bound to its Target, σ$^{28}$," Nature Structural Biology 4(4):285-291, Nature Publishing Group, United States (1997).

Dobo, J., et al., "Application of a Short, Disordered N-terminal Flagellin Segment, A Fully Functional Flagellar Type III Export Signal, to Expression of Secreted Proteins," Applied and Environmental Microbiology 76(3):891-899, American Society for Microbiology, United States (2010).

Dorel, C., et al., "The Cpx System of *Escherichia coli*, A Strategic Signaling Pathway for Confronting Adverse Conditions and for Settling Biofilm Communities?," Research in Microbiology 157(4):306-314, Elsevier, France (2006).

Dudley, S.C., et al., "A μ-conotoxin-insensitive Na$^+$ Channel Mutant: Possible Localization of a Binding Site at the Outer Vestibule," Biophysical Journal 69(5):1657-1665, Cell Press, United States (1995).

Ellermeier, C.D. and Slauch, J.M., "RtsA and RtsB Coordinately Regulate Expression of the Invasion and Flagellar Genes in *Salmonella enterica* Serovar Typhimurium," Journal of Bacteriology 185(17):5096-5108, American Society for Microbiology, United States (2003).

Enomoto, M. and Stocker, B.A., "Integration, at Hag or elsewhere, of H2 (Phase-2 Flagellin) Genes Transduced from *Salmonella* to *Escherichia coli*," Genetics 81(4):595-614, Genetics Society of America, United States (1975).

Erhardt, M. and Hughes, K.T., "C-ring Requirement in Flagellar Type III Secretion is Bypassed by FlhDC Upregulation," Molecular Microbiology 75(2):376-393, Blackwell Scientific Publications, England (2010).

Erhardt, M., et al., "Bacterial Nanomachines: The Flagellum and Type III Injectisome," Cold Spring Harbor Perspectives in Biology 2(11):a000299, Cold Spring Harbor Laboratory Press, United States (2010).

Fattori, J., et al., "Bacterial Secretion Chaperones," Protein and Peptide Letters 18(2):158-166, Bentham Science Publishers, Netherlands (2011).

Fiedler, B., et al., "Specificity, Affinity and Efficacy of Iota-conotoxin RXIA, An Agonist of Voltage-gated Sodium Channels Na$_v$1.2, 1.6 and 1.7," Biochemical Pharmacology 75(12):2334-2344, Elsevier Science, England (2008).

Flynn, J.M., et al., "Proteomic Discovery of Cellular Substrates of the ClpXP Protease Reveals Five Classes of ClpX-recognition Signals," Molecular Cell 11(3):671-683, Cell Press, United States (2003).

Francez-Charlot, A., et al., "RcsCDB His-Asp Phosphorelay System Negatively Regulates the flhDC Operon in *Escherichia coli*," Molecular Microbiology 49(3):823-832, Blackwell Scientific Publications, England (2003).

Fraser, G.M., et al., "Substrate-specific Binding of Hook-associated Proteins by FlgN and FliT, Putative Chaperones for Flagellum Assembly," Molecular Microbiology 32(3):569-580, Blackwell Scientific Publications, England (1999).

Frye, J., et al., "Identification of New Flagellar Genes of *Salmonella enterica* Serovar Typhimurium," Journal of Bacteriology 188(6):2233-2243, American Society for Microbiology, United States (2006).

Galan, J.E. and Curtiss, R., "Expression of *Salmonella typhimurium* Genes Required for Invasion is Regulated by Changes in DNA Supercoiling," Infection and Immunity 58(6):1879-1885, American Society for Microbiology, United States (1990).

Gillen, K.L. and Hughes, K.T., "Molecular Characterization of flgM, A Gene Encoding a Negative Regulator of Flagellin Synthesis in *Salmonella typhimurium*," Journal of Bacteriology 173(20):6453-6459, American Society for Microbiology, United States (1991).

Gillen, K.L. and Hughes, K.T., "Transcription from Two Promoters and Autoregulation Contribute to the Control of Expression of the *Salmonella typhimurium* Flagellar Regulatory Gene flgM," Journal of Bacteriology 175(21):7006-7015, American Society for Microbiology, United States (1993).

Green, B.R., et al., "Conotoxins Containing Nonnatural Backbone Spacers: Cladistic-based Design, Chemical Synthesis, and Improved Analgesic Activity," Chemistry and Biology 14(4):399-407, Elsevier, United States (2007).

Hughes, K.T., et al., "Sensing Structural Intermediates in Bacterial Flagellar Assembly by Export of a Negative Regulator," Science 262(5137):1277-1280, American Association for the Advancement of Science, United States (1993).

Hughes, K.T., et al., "The *Salmonella typhimurium* nadC Gene: Sequence Determination by Use of Mud-P22 and Purification of Quinolinate Phosphoribosyltransferase," Journal of Bacteriology 175(2):479-486, American Society for Microbiology, United States (1993).

Hui, K., et al., "Electrostatic and Steric Contributions to Block of the Skeletal Muscle Sodium Channel by μ-conotoxin," Journal of General Physiology 119(1):45-54, Rockefeller University Press, United States (2002).

Ikebe, T., et al., "Structure and Expression of the fliA Operon of *Salmonella typhimurium*," Microbiology 145(Pt 6):1389-1396, Kluwer Academic/Plenum Publishers, United States (1999).

International Searching Authority, International Search Report for International Application No. PCT/US13/43384, ISA/US, Alexandria, Virginia, United States, dated Oct. 25, 2013, 4 pages.

Iyoda, S., et al., "A Flagellar Gene fliZ Regulates the Expression of Invasion Genes and Virulence Phenotype in *Salmonella enterica* Serovar Typhimurium," Microbial Pathogenesis 30(2):81-90, Academic Press, England (2001).

Jones, R.M. and Bulaj, G., "Conotoxins—New Vistas for Peptide Therapeutics," Current Pharmaceutical Design 6(12):1249-1285, Bentham Science Publishers, Netherlands (2000).

Karlinsey, J.E., et al., "Completion of the Hook-basal Body Complex of the *Salmonella typhimurium* Flagellum is Coupled to FlgM Secretion and fliC Transcription," Molecular Microbiology 37(5):1220-1231, Blackwell Scientific Publications, England (2000).

Karlinsey, J.E., et al., "Translation/secretion Coupling by Type III Secretion Systems," Cell 102(4):487-497, Cell Press, United States (2000).

(56) References Cited

OTHER PUBLICATIONS

Karlinsey, J.E., "lambda-Red Genetic Engineering in Salmonella enterica Serovar Typhimurium," in 421 Methods in Enzymology, Advanced Bacterial Genetics: Use of Transposons and Phage for Genomic Engineering, 199-209 (Kelly T. Hughes and Stanley R. Maloy eds., Academic Press 2007), United States.
Kutsukake, K., "Excretion of the Anti-sigma Factor through a Flagellar Substructure Couples Flagellar Gene Expression with Flagellar Assembly in Salmonella typhimurium," Molecular and General Genetics 243(6):605-612, New York Springer-Verlag, Germany (1994).
Lee, H.J. and Hughes, K.T., "Posttranscriptional Control of the Salmonella enterica Flagellar Hook Protein FlgE," Journal of Bacteriology 188(9):3308-3316, American Society for Microbiology, United States (2006).
Lehnen, D., et al., "LrhA as a New Transcriptional Key Regulator of Flagella, Motility and Chemotaxis Genes in Escherichia coli," Molecular Microbiology 45(2):521-532, Blackwell Scientific Publications, England (2002).
Lemke, J.J., et al., "DksA and ppGpp Directly Regulate Transcription of the Escherichia coli Flagellar Cascade," Molecular Microbiology 74(6):1368-1379, Blackwell Scientific Publications, England (2009).
Lucas, R.L., et al., "Multiple Factors Independently Regulate hilA and Invasion Gene Expression in Salmonella enterica Serovar Typhimurium," Journal of Bacteriology 182(7):1872-1882, American Society for Microbiology, United States (2000).
Macnab, R.M., "How Bacteria Assemble Flagella," Annual Review of Microbiology 57:77-100, Annual Reviews, United States (2003).
Macnab, R.M., "Type III Flagellar Protein Export and Flagellar Assembly," Biochimica et Biophysica Acta 1694(1-3):207-217, Elsevier, Netherlands (2004).
Merdanovic, M., et al., "Protein Quality Control in the Bacterial Periplasm," Annual Review of Microbiology 65:149-168, Annual Reviews, United States (2011).
Miljanich, G.P., "Venom Peptides as Human Pharmaceuticals," Science and Medicine 4(5):6-15, Science and Medicine, Inc., United States(1997).
Miljanich, G.P., "Ziconotide: Neuronal Calcium Channel Blocker for Treating Severe Chronic Pain," Current Medicinal Chemistry 11(23):3029-3040, Bentham Science Publishers, Netherlands (2004).
Minamino, T. and Namba, K., "Distinct Roles of the FliI ATPase and Proton Motive Force in Bacterial Flagellar Protein Export," Nature 451(7177):485-488, Nature Publishing Group, England (2008).
Nakamura, M., et al., "Modification of Arg-13 of μ-conotoxin GIIIA with Piperidinyl-Arg Analogs and their Relation to the Inhibition of Sodium Channels," FEBS Letters 503(1):107-110, Elsevier Science B.V., Netherlands (2001).
Namba, K., "Roles of Partly Unfolded Conformations in Macromolecular Self-assembly," Genes to Cells 6(1):1-12, Blackwell Scientific Publications, England (2001).
Ohnishi, K., et al., "A Novel Transcriptional Regulation Mechanism in the Flagellar Regulon of Salmonella typhimurium: An Antisigma Factor Inhibits the Activity of the Flagellum-specific Sigma Factor, σF," Molecular Microbiology 6(21):3149-3157, Blackwell Scientific Publications, England (1992).
Ohnishi, K., et al., "Gene fliA Encodes an Alternative Sigma Factor Specific for Flagellar Operons in Salmonella typhimurium," Molecular and General Genetics 221(2):139-147, New York Springer-Verlag, Germany (1990).
Olivera, B.M., "ω-Conotoxin MVIIA: From Marine Snail Venom to Analgesic Drug," in Drugs From the Sea 74-85, Nobuhiro Fusetani ed., Karger 2000), Switzerland.
Osterberg, S., et al., "Regulation of Alternative Sigma Factor Use," Annual Review of Microbiology 65:37-55, Annual Reviews, United States (2011).
Paul, K., et al., "Energy Source of Flagellar Type III Secretion," Nature 451(7177):489-492, Nature Publishing Group, England (2008).

Sanderson, K.E. and Roth, J.R., "Linkage Map of Salmonella typhimurium, Edition VI," Microbiological Reviews 47(3):410-453, American Society for Microbiology, United States (1983).
Singer, H.M., et al., "Selective Purification of Recombinant Neuroactive Peptides Using the Flagellar Type III Secretion System," mBio 3(3):e00115-12, American Society for Microbiology, United States (2012).
Sorenson, M.K., et al., "Crystal Structure of the Flagellar σ/anti-σ Complex σ (28)/FlgM Reveals an Intact σ Factor in an Inactive Conformation," Molecular Cell 14(1):127-138, Cell Press, United States (2004).
Sourjik, V. and Wingreen, N.S., "Responding to Chemical Gradients: Bacterial Chemotaxis," Current Opinion in Cell Biology 24(2):262-268, Elsevier, England (2012).
Takaya, A., et al., "YdiV: A Dual Function Protein that Targets FlhDC for ClpXP-dependent Degradation by Promoting Release of DNA-bound FlhDC Complex," Molecular Microbiology 83(6):1268-1284, Blackwell Scientific Publications, England (2012).
Terlau, H. and Olivera, B.M., "Conus Venoms: A Rich Source of Novel Ion Cchannel-targeted Peptides," Physiological Reviews 84(1):41-68, American Physiological Society, United States (2004).
Tomoyasu, T., et al., "The ClpXP ATP-dependent Protease Regulates Flagellum Synthesis in Salmonella enterica Serovar Typhimurium," Journal of Bacteriology 184(3):645-653, American Society for Microbiology, United States (2002).
Wada, T., et al., "EAL Domain Protein YdiV Acts as an Anti-FlhD4C2 Factor Responsible for Nutritional Control of the Flagellar Regulon in Salmonella enterica Serovar Typhimurium," Journal of Bacteriology 193(7):1600-1611, American Society for Microbiology, United States (2011).
Wang, Q., et al., "The RcsCDB Signaling System and Swarming Motility in Salmonella enterica Terovar typhimurium: Dual Regulation of Flagellar and SPI-2 Virulence Genes," Journal of Bacteriology 189(23):8447-8457, American Society for Microbiology, United States (2007).
Wang, S., et al., "Structure of the Escherichia coli FlhDC Complex, A Prokaryotic Heteromeric Regulator of Transcription," Journal of Molecular Biology 355(4):798-808, Elsevier, England (2006).
Wei, B.L., et al., "Positive Regulation of Motility and flhDC Expression by the RNA-binding Protein CsrA of Escherichia coli," Molecular Microbiology 40(1):245-256, Blackwell Scientific Publications, England (2001).
Wozniak, C.E., et al., "T-POP Array Identifies EcnR and PefI-SrgD as Novel Regulators of Flagellar Gene Expression," Journal of Bacteriology 191(5):1498-1508, American Society for Microbiology, United States (2009).
International Searching Authority, Written Opinion for International Application No. PCT/US13/43384, ISA/US, Alexandria, Virginia, United States, dated Oct. 25, 2013, 5 pages.
Yamamoto, S. and Kutsukake, K., "FliT Acts as An Anti-FlhD2C2 Factor in the Transcriptional Control of the Flagellar Regulon in Salmonella enterica Serovar Typhimurium," Journal of Bacteriology 188(18):6703-6708, American Society for Microbiology, United States (2006).
Yanagihara, S., et al., "Structure and Transcriptional Control of the Flagellar Master Operon of Salmonella typhimurium," Genetics Society of Japan, Japan 74(3):105-111, Genes and Genetic Systems (1999).
Yao, S., et al., "Structure, Dynamics, and Selectivity of the Sodium Channel Blocker mu-conotoxin SIIIA," Biochemistry 47(41):10940-10949, American Chemical Society, United States (2008).
Yokoseki, T., et al., "Functional Analysis of the Flagellar Genes in the fliD Operon of Salmonella typhimurium," Microbiology 141(Pt 7):1715-1722, Kluwer Academic/Plenum Publishers, United States (1995).
Jie Zhang, Fusion to FLGM Allows Secretion and Purification of Conotoxin Protein Through the Flagellar Type III Secretion System (Dec. 2008) (M.S. thesis, The University of Utah; available at Marriott Library Special Collections).
Berger, E., et al., "Extracellular secretion of a recombinant therapeutic peptide by Bacillus halodurans utilizing a modified flagellin type III secretion system," Microbial Cell Factories 10(62):1-10 (2011), BioMed Central Ltd., England.

(56) References Cited

OTHER PUBLICATIONS

Vonderviszt, F., et al., "The Use of a Flagellar Export Signal for the Secretion of Recombinant Proteins in *Salmonella*," in 824 Recombinant Gene Expression: Reviews and Protocols, Third Edition, Methods in Molecular Biology 131-143 (Angelia Lorence, ed., 2012), Humana Press, United States.
Extended European Search Report of European Appl. No. 13798228.6, European Patent Office, Munich, Germany, dated Mar. 4, 2016, 5 pages.
Aldridge, P.D., et al., "The flagellar-specific transcription factor, σ28, is the Type III secretion chaperone for the flagellar-specific anti-σ28 factor FlgM," Genes & Development 20:2315-2326, Cold Harbor Springs Laboratory Press, United States (2006).
Mizusaki, H., et al., "Signal Pathway in Salt-Activated Expression of the *Salmonella* Pathogenicity Island 1 Type III Secretion System in *Salmonella enterica* Serovar Typhimurium," Journal of Bacteriology 190(13):4624-4631, American Society for Microbiology, United States (2008).
Widmaier, D.M., et al., "Engineering the *Salmonella* type III secretion system to export spider silk monomers," Molecualr Systems Biology 5:309, 9 pages, Wiley Blackwell, England (2009).
Salto, T. et al., "Flagellar filament elongation can be impaired by mutations in the hook protein FlgE of *Salmonella typhimurium*: a possible role of the hook as a passage for the anti-stigma factor FlgM," Molecular Microbiology 26(6):1129-1139, Wiley-Blackwell, United States (1998).
Grosjean, H. et al. "Deciphering synonymous codons in the three domains of life: co-evolution with specific tRNA modification enzymes," FEBS Lett. 584:252-264 (2010).
Goodman, D. B., et al., "Causes and effects of N-terminal codon bias in bacterial genes," Science 342:475-478 (2013).
Nei, M. "Selectionism and neutralism in molecular evolution," *Mol. Biol. Evol.* 22:2318-2342 (2005).
Hunt, R. C., et al.,"Exposing synonymous mutations," Trends Genet. 30:308-321 (2014).
Sauna, Z. E., et al., "Understanding the contribution of synonymous mutations to human disease," Nat Rev Genet 12:683-91 (2011).
Supek, F., et al., "Synonymous mutations frequently act as driver mutations in human cancers," Cell 156:1324-35 (2014).
International Searching Authority, International Search Report for International Application No. PCT/US2016/055162, ISA/US, Alexandria, Virginia, United States, dated Jan. 9, 2017, 4 pages.
International Searching Authority, Written Opinion for International Application No. PCT/US2016/055162, ISA/US, Alexandria, Virginia, United States, dated Jan. 9, 2017, 5 pages.
Chevance et al. "The effects of codon context on in vivo translation speed," PLoS Genet. 05 1-16, 28-35, 49-54 (Jun. 2014).
Non-Final Office Action for U.S. Appl. No. 14/404,919, filed Dec. 1, 2014, dated Sep. 30, 2015, 7 pages.
Final Office Action for U.S. Appl. No. 14/404,919, filed Dec. 1, 2014, dated Apr. 18, 2016, 10 pages.
Den Bakker et al. "Transcription termination protein NusA [*Salmonella enterica* subsp. *enterica* serovar Inverness str. R8-3668]," Retrieved from the Internet: URL: https://www.ncbi.nlm.nih.gov/protein/EHC51912. Oct. 21, 2011.
Supplementary European Search Report and European Search Opinion for EP Application No. 16852823.0, The Hague, Netherlands, dated Feb. 26, 2019.

\* cited by examiner

| Thr6 \ Pro8 | CCU | CCC | CCA | CCG |
|---|---|---|---|---|
| ACU | 11±1.6 | 14±2.7 | 12±2.6 | 34±6.4 |
| ACC | 1.0±0.15 | 1.7±0.3 | 1.4±0.2 | .053±0.004 |
| ACA | 13±1.9 | 14±2.3 | 12±2.3 | 11±2.1 |
| ACG | 13±2.1 | 14±2.7 | 11±2.1 | 6±1.3 |

FIG. 2

Synonymous Changes That Suppress The Pro8 Translation Defect

Thr6:
ACC->ACA (6)
ACC->ACG (1)
ACC->ACT (3)

Ser7:
TCA->TCG (6)
TCA->TCC (6)
TCA->TCT (2)

Leu9:
TTG->TTA (3)

FlgM

MSIDRTSPLKPVSTVQTRETSDTPVQKTRQEKTSAATSASVTLSDAQAKLMQPGVSDINMERVEALKTAIRNGELKMDTGKIADSLIREAQSYLQSK*

Ser2
ACG->AGT

Pro8
CCG

Asp4
GAC->GAT

Thre6:
ACC->Δ (2)

Val12
GTT->GTG (2)
GTT->GTC (1)

Val25
CCG->CCC (2)

Pro24
CCG->CCC

Thre23
AGC->ACA

Ser21
AGC->AGT

Thre20
ACC->ACA
ACC->ACG

Gln16
CAG->CAA

Val15
GTC->GTG

Synonymous Changes With No (or slight) Phenotypic Change

FIG. 3

COMPOSITIONS FOR ADJUSTABLE RIBOSOME TRANSLATION SPEED AND METHODS OF USE

The sequence listing was submitted with this application on Mar. 30, 2018. Please incorporate the text copy of the Sequence Listing by reference that was filed on Mar. 30, 2018.

BACKGROUND OF THE INVENTION

In 1961, Crick et al. published their landmark *Nature* paper, "General nature of the genetic code for proteins" (Crick, F. H., et al. *Nature* 192:1227-32 (1961)). Using a simple, yet clever genetic approach of combining +1 and −1 frameshift mutations, Crick et al. provided evidence for the triplet code that is part of the central dogma of molecular biology: DNA is transcribed into mRNA by RNA polymerase, which is translated into protein by ribosomes. The genetic code for the amino acid sequences of proteins is composed of 64 triplet codons that specify the twenty amino acids and sites of translation termination (stop codons). The interaction between a specific codon in the mRNA being translated and the three bases that define the anticodon of the cognate aminoacyl-tRNA (bases 36, 35 and 34 within the anticodon loop) determines the decoding process (Grosjean, H., et al., *FEBS Lett.* 584:252-264 (2010)).

It is now known that the decoding process is more complicated. The ability of the ribosome to translate a given codon is highly influenced by its neighboring codons (referred to as the codon context effect on translation) and perhaps mRNA secondary structure (Goodman, D. B., et al., *Science* 342:475-478 (2013)). Translation of a given codon is also influenced by the location of the codon within the mRNA open reading frame. Further, while synonymous mutations (nucleotide changes within the codon that do not change the encoded amino acid) were long thought to be evolutionarily silent (Nei, M. *Mol. Biol. Evol.* 22:2318-2342 (2005)), it is now known that synonymous codons affect translation speed and accuracy, co-translational folding, protein secretion and overall expression levels (Hunt, R. C., et al., *Trends Genet.* 30:308-321 (2014)). Recent evidence supports an association between mutations resulting in synonymous codons and human diseases such as cancer (Sauna, Z. E., and C. Kimchi-Sarfaty, *Nat Rev Genet* 12:683-91 (2011); Supek, F., et al., *Cell* 156:1324-35 (2014)).

BRIEF SUMMARY OF THE INVENTION

The present invention provides synonymous changes in codons pairs that result in differing ribosome translation speed and accuracy, protein folding and expression. In one embodiment, the invention provides a 15-base pair sequence for manipulation of expression of proteins in genetically modified organisms. The present invention also provides a method to screen for polynucleotide mutations that result in deleterious effects associated with disease states.

In one embodiment, the present invention provides engineered FlgM coding sequences, or ten-codon-fragments thereof, that, when appended to a heterologous polynucleotide sequence encoding a desired protein, increases or decreases the translation efficiency of that protein which results in modulated production of a polypeptide of interest.

In one embodiment, the present invention further utilizes a bacterial secretion system (such as the flagellar type III secretion (T3S) system (T3SS)) to secrete the desired protein into culture media and therefore provide a protein production method that is more efficient than a method requiring cell lysis for protein recovery.

The present invention also provides a recombinant nucleic acid molecule comprising a mutant triacontanucleotide sequence having ten codons, wherein at least one of the sixth, seventh, eighth, ninth and tenth codons, in the 5' to 3' direction, are synonymous codons. In certain embodiments, the recombinant nucleic acid molecule consists of a mutant triacontanucleotide sequence. In another embodiment, the mutant triacontanucleotide sequence encodes the amino acid sequence MSIDRTSPLK (SEQ ID NO:1). In other embodiments, the mutant triacontanulcoetide sequence is part of a sequence that encodes the full-length FlgM amino acid sequence:

```
                                        (SEQ ID NO: 3)
MSIDRTSPLKPVSTVQTRETSDTPVQKTRQEKTSAATSASVTLSD

AQAKLMQPGVSDINMERVEALKTAIRNGELKMDTGKIADSLIREA

QSYLQSK.
```

In one embodiment, the mutant triacontanucleotide sequence is operably linked to a polynucleotide sequence that encodes a polypeptide of interest. In another embodiment, the mutant triacontanucleotide sequence is operably linked, in the 5' to 3' direction, to a polynucleotide sequence that encodes a polypeptide of interest. In certain embodiments, the mutant triacontanucleotide sequence encodes the amino acid sequence SEQ ID NO: 3 and is operably linked, in the 5' to 3' direction, to a polynucleotide sequence that encodes a polypeptide of interest.

In one embodiment, the mutant triacontanucleotide sequence is further operably linked to a cleavage site nucleotide sequence. In one embodiment, the cleavage site encodes a Tobacco Etch Virus (TEV) protease cleavage site or an Enterokinase (ETK) cleavage site. In another embodiment, the mutant triacontanucleotide sequence is operably linked to a cleavage site nucleotide sequence and a polynucleotide sequence that encodes a polypeptide.

In one embodiment, the mutant triacontanucleotide sequence replaces the ten 5'-most codons of a polynucleotide sequence that encodes a polypeptide of interest. In one embodiment, the polypeptide of interest is heterologous to the mutant triacontanucleotide sequence.

In one embodiment, the mutant triacontanucleotide sequence is a ribonucleic acid sequence. In another embodiment, the mutant triacontanucleotide sequence is a deoxyribonucleic acid sequence.

In one embodiment, the mutant triacontanucleotide sequence is a synthetic sequence.

In one embodiment, the sixth and eighth codons of the mutant triacontanucleotide sequence, in the 5' to 3' direction, are synonymous codons.

In one embodiment, a vector comprises a mutant sequence of the invention. In another embodiment, the vector is an expression vector.

In one embodiment, a vector comprises the mutant triacontanucleotide sequence operably linked to a polynucleotide sequence that encodes a polypeptide of interest and is operably linked to a nucleotide sequence that encodes a cleavage site. In another embodiment, the cleavage site nucleotide sequence is between the mutant triacontanucleotide sequence and the polynucleotide sequence of interest. In another embodiment the vector further comprises a nucleic acid sequence encoding a purification tag wherein the nucleic acid sequence is operably linked to the mutant triacontanucleotide sequence.

In one embodiment, the mutant triacontanucleotide sequence is operably linked to a polynucleotide sequence encoding a polypeptide of interest, a nucleic acid sequence encoding a purification tag, and, optionally, a nucleotide sequence encoding a cleavage site.

In one embodiment, the mutant triacontanucleotide sequence or polynucleotide sequence is operably linked to a heterologous promoter. In another embodiment, the promoter is an inducible promoter, a constitutive promoter, or a tissue specific promoter. An inducible promoter of the present invention may be an arabinose inducible promoter such as the ParaBAD (ΔaraBAD) promoter or a salycilate inducible promoter such as the Psal promoter. In one embodiment, a host cell comprises the recombinant molecule. In another embodiment, the host cell is a bacterial, fungal, yeast, viral, plant, insect, or mammalian cell. In another embodiment, the host cell is a *Salmonella* or *Escherichia coli* cell. In another embodiment, the host cell is a *Salmonella enterica* cell. In one embodiment, the mutant triacontanucleotide sequence operably linked to the polynucleotide sequence, which is optionally further operably linked to a cleavage site, is operatively integrated into the host cell genome.

In one embodiment, a host cell comprises a vector of the invention.

In one embodiment, the polynucleotide sequence within the vector has been codon optimized for expression within a host cell.

The present invention provides a recombinant molecule comprising a nucleic acid sequence having ten codons, wherein at least one of the sixth, seventh, eighth, ninth and tenth codons, in the 5' to 3' direction, are synonymous codons. In one embodiment, the nucleic acid sequence is operably linked to a polynucleotide sequence.

The present invention provides a recombinant nucleic acid molecule having a modulated translation speed, comprising the decacodon sequence 5'-AUGAGCAUUGACCGUACCUCACCUUUGAAA-3' (SEQ ID NO:2), wherein at least one of the sixth, seventh, eighth, ninth and tenth codons, in the 5' to 3' direction, are synonymous codons. In certain embodiments, the nucleic acid molecule comprises this nucleic acid sequence and encodes the amino acid sequence SEQ ID NO: 3.

In one embodiment, the sixth codon is the synonymous codon ACU, ACA, or ACG and wherein the recombinant molecule has increased translation speed as compared to a molecule comprising the decacodon sequence. In one embodiment, the sixth codon is a synonymous codon and the molecule has between about a 5- to about 15-fold increase in translation speed as compared to a molecule comprising the native decacodon sequence. In another embodiment, the molecule has between about a 9- to about 15-fold increase in translation speed as compared to a molecule comprising the native decacodon sequence.

In one embodiment, the eighth codon is the synonymous codon CCG and wherein the recombinant molecule has decreased translation speed as compared to a molecule comprising the native decacodon sequence. In one embodiment, the eighth codon is a synonymous codon and the recombinant molecule has between about a 0.01 to about 0.10-fold decrease in translation speed as compared to a molecule comprising the native decacodon sequence. In another embodiment, the molecule has between about a. 0.03- to about 0.07-fold decrease in translation speed as compared to a molecule comprising the native decacodon sequence.

In one embodiment, the sixth codon is the synonymous codon ACU, the eighth codon is the synonymous codon CCG, and wherein the recombinant molecule has increased translation speed as compared to a molecule comprising the native decacodon sequence. In one embodiment, the sixth codon is a synonymous codon, the eighth codon is a synonymous codon, and wherein the recombinant molecule has between about a 10- to 50-fold increase in translation speed as compared to a molecule comprising the native decacodon sequence. In another embodiment, the molecule has between about a 20- to about 50-fold increase in translation speed. In another embodiment, the molecule has between about a 30- to about 50-fold increase in translation speed. In another embodiment, the molecule has between about a 40- to about 50-fold increase in translation speed. In another embodiment, the molecule has between about a 27.5- to 40.5-fold increase in translation speed as compared to a molecule comprising the native decacodon sequence.

In one embodiment, the decacodon sequence is operably linked to a polynucleotide sequence that encodes a polypeptide of interest.

The present invention provides a method of modulating protein production within a host cell, comprising culturing a host cell of the invention under conditions sufficient for protein expression, wherein a recombinant nucleic acid molecule has been stably introduced into the host cell. In one embodiment, the recombinant nucleic acid molecule comprises a mutant triacontanucleotide sequence having ten codons, wherein at least one of the sixth, seventh, eighth, ninth and tenth codons, in the 5' to 3' direction, are synonymous codons. In one embodiment, the recombinant molecule comprises a nucleic acid sequence having ten codons, wherein at least one of the sixth, seventh, eighth, ninth and tenth codons, in the 5' to 3' direction, are synonymous codons. In another embodiment, the nucleic acid sequence comprising the synonymous codons encodes the amino acid sequence SEQ ID NO: 3.

In one embodiment, the sixth codon is the synonymous codon ACU, ACA, or ACG and wherein protein production is increased as compared to a corresponding host cell utilizing wild type triacontanucleotide sequence. In one embodiment, the sixth codon is a synonymous codon and the molecule has between about a 5- to about 15-fold increase in protein production as compared to a corresponding host cell utilizing a wild type triacontanucleotide sequence. In another embodiment, the molecule has between about a 9- to about 15-fold increase in protein production as compared to a corresponding host cell utilizing a wild type triacontanucleotide sequence.

In one embodiment, the eighth codon is the synonymous codon CCG and wherein protein production is decreased as compared to a corresponding host cell utilizing a wild type triacontanucleotide sequence. In one embodiment, the eighth codon is a synonymous codon and the recombinant molecule has between about a 0.01 to about 0.10-fold decrease in protein production as compared to a corresponding host cell utilizing a wild type triacontanucleotide sequence. In another embodiment, the molecule has between about a 0.03- to about 0.07-fold decrease in protein production as compared to a corresponding host cell utilizing a wild type triacontanucleotide sequence.

In one embodiment, the sixth codon is the synonymous codon ACU, the eighth codon is the synonymous codon CCG, and wherein protein production is increased as compared to a corresponding host cell utilizing wild type triacontanucleotide sequence.

In one embodiment, the sixth codon is a synonymous codon, the eighth codon is a synonymous codon, and wherein the recombinant molecule has between about a 10- to 50-fold increase in protein production as compared to a corresponding host cell utilizing a wild type triacontanucleotide sequence. In another embodiment, the molecule has between about a 20- to about 50-fold increase in protein production as compared to a corresponding host cell utilizing a wild type triacontanucleotide sequence. In another embodiment, the molecule has between about a 30- to about 50-fold increase in protein production as compared to a corresponding host cell utilizing a wild type triacontanucleotide sequence. In another embodiment, the molecule has between about a 40- to about 50-fold increase in protein production as compared to a corresponding host cell utilizing a wild type triacontanucleotide sequence. In another embodiment, the molecule has between about a 27.5- to 40.5-fold increase in protein production as compared to a corresponding host cell utilizing a wild type triacontanucleotide sequence.

The present invention provides a method of increasing the translation speed of a polynucleotide sequence, comprising providing a polynucleotide sequence that encodes a protein and is operably linked to a wild type triacontanucleotide sequence wherein the triacontanucleotide sequence comprises ten codons and encodes MSIDRTSPLK (SEQ ID NO:1), and mutating the triacontanucleotide sequence so that at least one of the sixth, seventh, eighth, ninth and tenth codons, in the 5' to 3' direction, are synonymous codons. In further embodiments, the wild type triacontanucleotide sequence and the mutant triacontanucleotide sequence encode the amino acid sequence SEQ ID NO: 3.

In one embodiment, the sixth codon of the resulting mutant triacontanucleotide sequence comprises the synonymous codon ACU, ACA, or ACG and wherein translation speed of the polynucleotide sequence is increased compared to translation under the control of the wild type triacontanucleotide sequence.

In one embodiment, the eighth codon of the resulting mutant triacontanucleotide sequence comprises the synonymous codon CCG and wherein translation speed of the polynucleotide sequence is decreased compared to translation under the control of the wild type triacontanucleotide sequence.

In one embodiment, the sixth codon is the synonymous codon ACU, the eighth codon is the synonymous codon CCG, and wherein translation speed of the polynucleotide sequence is increased compared to translation under the control of the wild type triacontanucleotide sequence.

The present invention provides a method of producing polypeptides of interest comprising culturing a host cell that contains a mutant triacontanucleotide sequence operably linked to a polynucleotide sequence encoding the polypeptide of interest. In one embodiment, the mutant triacontanucleotide sequence and polynucleotide sequence are operably linked to a nucleotide sequence encoding a cleavage site and/or a nucleic acid sequence encoding a purification tag. In one embodiment, the peptide is purified from the culture media. In one embodiment, the purification tag is utilized to purify the peptide from the culture media. In one embodiment, the triacontanucleotide sequence encodes the FlgM protein having the amino acid sequence SEQ ID NO: 3 and the peptide is isolated from the FlgM protein. In another embodiment, the cleavage site is utilized to isolate the polypeptide from the FlgM protein.

The present invention provides a method of producing polypeptides of interest comprising culturing one or more bacterial cells having a Type III Secretion System and also contain a mutant triacontanucleotide sequence operably linked to a heterologous polynucleotide sequence that encodes a desired polypeptide, and wherein the polypeptide is secreted into the culture media. In one embodiment, the bacterial cells are either *Salmonella* or *Escherichia* cells. In one embodiment, the triacontanucleotide sequence encodes a full-length FlgM peptide. In one embodiment, the triacontanucleotide sequence and polynucleotide sequence are operably linked to a nucleotide sequence encoding a purification tag and/or a cleavage site. In one embodiment, the method utilizes is a continuous flow manufacturing system for production of the polypeptide of interest. In one embodiment, the continuous flow manufacturing system produces insulin, MaSp1, or MaSp2 protein.

BRIEF DESCRIPTION OF THE DRAWINGS/FIGURES

FIG. 1 depicts the *Salmonella enterica* flagellum gene regulation coupled to assembly.

FIG. 2 depicts the effect of synonymous changes at codons Thr6 and Pro8 of flgM on FlgM anti-$\sigma^{28}$ activity in exponential cultures. Data is presented as levels of FlgM anti-$\sigma^{28}$ activity. Wild-type codon (ACC) exhibited the lowest FlgM activity/luciferase activity for each of the 15 combinations of synonymous Thr6 and Pro8 codons assayed.

FIG. 3 depicts the effects of synonymous codon mutagenesis on suppression of the Pro8 CCG translation-defective allele of flgM. Mutants that showed wild-type FlgM activity on indicator medium are shown above the FlgM sequence (SEQ ID NO: 3). Mutants with slightly increased FlgM activity are Ser2 (ACG to AGT), Thre6 (ACC to stop), Val 12 (GTT to GTG and GTT to GTC). The remaining mutants depicted below the FlgM sequence (ten isolates) had no phenotype. The number in parenthesis denotes the number of repeats.

Figure 4:
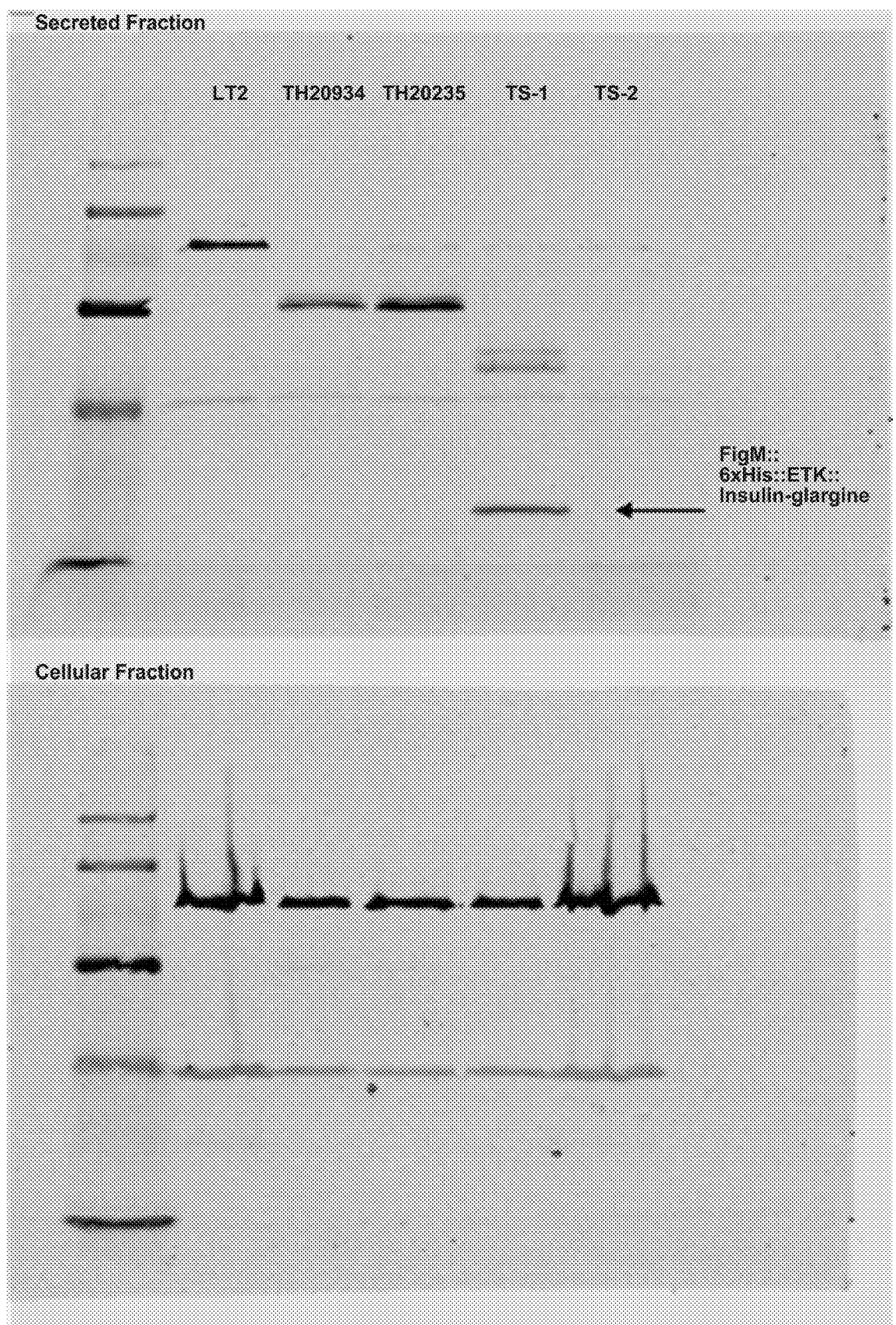

FIG. 4 depicts the detection of FlgM::6×His::ETK::Insulin-glargine chimeric proteins within secreted fractions (top) and cellular fractions (bottom) of engineered *Salmonella* cells via Western blot using anti-6×His antibodies.

DETAILED DESCRIPTION OF THE INVENTION

Definitions

To facilitate an understanding of the present invention, a number of terms and phrases are defined below. Art-recognized synonyms or alternatives of the following terms and phrases, even if not specifically described, are contemplated.

As used in the present disclosure and claims, the singular forms “a,” “an,” and “the” include plural forms unless the context clearly dictates otherwise; i.e., “a” means “one or more” unless indicated otherwise.

The terms “about” or “approximately” mean roughly, around, or in the regions of. The terms “about” or “approximately” further mean within an acceptable contextual error range for the particular value as determined by one of ordinary skill in the art, which will depend in part on how the value is measured or determined, i.e. the limitations of the measurement system or the degree of precision required for a particular purpose, e.g. the amount of a nutrient within a feeding formulation. When the terms "about" or "approximately" are used in conjunction with a numerical range, it modifies that range by extending the boundaries above and below the numerical values set forth. For example "between about 5.5 to 6.5 g/l" means the boundaries of the numerical range extend below 5.5 and above 6.5 so that the particular value in question achieves the same functional result as within the range. For example, "about" and "approximately" can mean within one or more than one standard deviation as per the practice in the art. Alternatively, "about" and "approximately" can mean a range of up to 20%, preferably up to 10%, more preferably up to 5%, and more preferably up to 1% of a given value.

The term "and/or" as used in a phrase such as "A and/or B" is intended to include "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless specified otherwise, all of the designations "A %-B %," "A-B %," "A % to B %," "A to B %," "A %-B," "A % to B" are given their ordinary and customary meaning. In some embodiments, these designations are synonyms.

The terms "substantially" or "substantial" mean that the condition described or claimed functions in all important aspects as the standard described. Thus, "substantially free" is meant to encompass conditions that function in all important aspects as free conditions, even if the numerical values indicate the presence of some impurities or substances. "Substantial" generally means a value greater than 90%, preferably greater than 95%, most preferably greater than 99%. Where particular values are used in the specification and in the claims, unless otherwise stated, the term "substantially" means with an acceptable error range for the particular value.

"Optional" or "optionally" means that the subsequently described event, circumstance, or material may or may not occur or be present, and that the description includes instances where the event, circumstance, or material occurs or is present and instances where it does not occur or is not present.

The terms "transformation" and "transfection" mean the introduction of a nucleic acid molecule (e.g., an expression vector) into a recipient cell. Transformation or transfection techniques are well known by the art. It may be specified that a nucleic acid sequence (e.g., a coding sequence carried by an expression vector) is introduced (integrated) into the genomic (chromosomal DNA) of said recipient (host) cell.

"FlgM" and "flgM" refers to the protein and polynucleotide sequence, respectively, that negatively regulates flagellin synthesis in Type III Secretion Systems (Gillen and Hughes, *Molecular Characterization of flgM, a Gene Encoding a Negative Regulator of Flagellin Synthesis in Salmonella typhimurium*, J. Bacteriology 173(20): 6453-6459 (1991)).

The term "recombinant" or "mutant" means that the referenced product has been altered with respect to its naturally occurring counterpart.

The term "triacontanucleotide sequence" means a nucleotide sequence that is at least thirty nucleotides long. For example, a triacontanucleotide sequence of the present invention may consist of thirty nucleotides or may be a part of a larger sequence, encoding for example, a full-length FlgM protein.

The term "codon" refers to the three consecutive nucleotides that together encode one amino acid.

The term "decacodon" means a nucleotide sequence comprising at least five codons (i.e., at least fifteen nucleotides). For example, a decacodon sequence of the present invention may consist of 10 codons or may comprise about 97 codons and encode a full-length FlgM peptide.

The term "synonymous codon" means a codon that is altered as compared to wild-type but that encodes the same amino acid as does the wild-type codon.

The terms "nucleic acid," "polynucleotide," and "nucleotide" are used synonymously herein. The term "polynucleotide," when used in singular or plural, generally refers to any a polyribonucleotide or polydeoxyribonucleotide, which can be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides. Polynucleotides can be made by a variety of methods, including in vitro recombinant DNA-mediated techniques and by expression of DNAs in cells and organisms The terms "protein," "polypeptide," and "peptide" are used synonymously herein. As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced by recombinant technology, but is not necessarily translated from a designated nucleic acid sequence. It can be generated in any manner, including by chemical synthesis. Certain embodiments of the present invention comprise a fusion peptide comprising at least a FlgM peptide and a polypeptide wherein the polypeptide and FlgM peptide do not naturally associate with each other (i.e., the polypeptide is heterologous to the FlgM peptide). Such a polypeptide may be referred to as a "heterologous polypeptide," a "target polypeptide," a "desired polypeptide" or a "polypeptides of interest."

An "isolated" biological component (such as a nucleic acid molecule or protein) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

The term "heterologous," "foreign" or "non-native" refers to two structures, for example, that are not naturally associated with each other. For example, wherein a nucleotide sequence is operably linked to a heterologous promoter, the nucleotide sequence is not naturally associated with the promoter even though the nucleotide sequence and the promoter sequence may originate from the same organism.

The terms "ribonucleic acid" and "RNA" are used herein synonymously.

The terms "deoxyribonucleic acid" and "DNA" are used herein synonymously.

A "vector" as used herein may be a cloning vector, an expression vector, a plasmid including a BAC or a YAC vector, or other nucleic acid molecule capable of transporting a polynucleotide sequence into a cell. A vector may be designed for storage of the polynucleotide sequence, cloning, and/or designed for expression of the polynucleotide sequence. "Plasmid" and "vector" may be used interchangeably, as a plasmid is a commonly used form of a vector. The term "expression vector" includes any vector, (e.g., a plasmid, cosmid or phage chromosome) containing a gene construct in a form suitable for expression by a cell (e.g., linked to a transcriptional control element). "Construct" or "gene construct" as used herein does not include an entire chromosomal and/or mitochondrial genome. Expression vectors suitable for use within a specified host cell are known and readily identified using routine experimentation and known techniques (see, e.g., U.S. Pat. Nos. 7,785,830; 8,663,980; 8,628,954, incorporated herein by reference in their entireties).

A "host cell" as used herein refers to a cell into which a molecule is or has been introduced. Generally, a host cell herein refers to a cell into which a foreign (heterologous, non-native) molecule is or has been introduced. In certain embodiments, the host cell herein is a bacterial cell. In certain embodiments, the host cell is a gram-negative bacterial cell. In certain embodiments, the host cell is a bacterial cell comprising a secretion system such as a Type III Secretion (T3S) System (T3SS). In certain embodiments, a host cell herein is selected from the group consisting of a *Salmonella, Shigella, Chlamydia, Yersinia, Pseudomonas,* and *Escherichia* cell. In certain embodiments, a host cell herein is selected from the group consisting of a *Salmonella enterica* serovar *Typhimurium, Shigella flexneri, Chlamydia trachomatis, Yersinia pseudotuberculosis, Pseudomonas aeruginosa,* and *Escherichia coli* cell.

A "purification tag" as used herein refers to a ligand that aids protein purification with, for example, size exclusion chromatography, ion exchange chromatography, and/or affinity chromatography. Purification tags and their use are well known to the art (see, e.g., Thermo Scientific Protein Purification Handbook 2010) and may be, for example, poly-histidine, glutathione S-transferase (GST), Myc, HA, FLAG, or maltose binding protein (MBP). A step of purifying, collecting, obtaining, or isolating a protein may therefore include size exclusion chromatography, ion exchange chromatography, or affinity chromatography. In certain embodiments, a step of purifying a FlgM peptide, or a fusion (chimeric) protein comprising FlgM, utilizes affinity chromatography and, for example, a $\sigma^{28}$ affinity column or an affinity column comprising an antibody that binds FlgM or another member of the fusion protein. In one embodiment, a step of purifying a fusion protein comprising at least a FlgM peptide and a purification tag utilizes affinity chromatography and, for example, an affinity column that binds the purification tag.

"Cleavage site" as used herein refers to a sequence that is recognized and/or cut by a chemical or protein (a restriction enzyme or protease, for example). Cleavage sites are well known by the art (see, e.g., US PG PUB NO. 2015/0037868, incorporated herein by reference in its entirety). Because cleavage sites may be polynucleotide sequences (e.g., restriction enzyme sites) or amino acid sequences (e.g., peptidase sites), a person with ordinary skill in the art will recognize, based on the context within which it is recited, whether "cleavage site" refers to a polynucleotide sequence or an amino acid sequence. Exemplary cleavage sites include those recognized by a protease selected from the group consisting of an alanine carboxypeptidase, *Armillaria mellea* astacin, bacterial leucyl aminopeptidase, cancer procoagulant, cathepsin B, clostripain, cytosol alanyl aminopeptidase, elastase, endoproteinase Arg-C, enterokinase, gastricsin, gelatinase, Gly-X carboxypeptidase, glycyl endopeptidase, human rhinovirus 3C protease, hypodermin C, Iga-specific serine endopeptidase, leucyl aminopeptidase, leucyl endopeptidase, lysC, lysosomal pro-X carboxypeptidase, lysyl aminopeptidase, methionyl aminopeptidase, myxobacter, nardilysin, pancreatic endopeptidase E, picornain 2A, picornain 3C, proendopeptidase, prolyl aminopeptidase, proprotein convertase I, proprotein convertase II, russellysin, saccharopepsin, semenogelase, T-plasminogen activator, thrombin, tissue kallikrein, tobacco etch virus (TEV), togavirin, tryptophanyl aminopeptidase, U-plasminogen activator, V8, venombin A, venombin AB, and Xaa-pro aminopeptidase. See US PG PUB NO. 2015/0037868, incorporated herein by reference in its entirety. In some embodiments, the cleavage site is a protease cleave site. In some embodiments, the cleavage site is a Tobacco Etch Virus (TEV) protease or Enterokinase (ETK) cleavage site. The components of a fusion (chimeric) peptide may be separated (released) via cutting at a cleavage site before, during, or after a step of fusion peptide purification. For example, wherein a fusion peptide comprises a FlgM protein fused to a heterologous polypeptide and a cleavage site, and the fusion peptide has been secreted into culture media, the FlgM protein and the polypeptide may be separated by the application of a protease to the culture media before a step of purification from culture media or the fusion peptide may be purified from the culture media and then a protease may be applied to the fusion peptide to release the FlgM protein from the polypeptide. In certain embodiments, a step of fusion peptide decomposition (cleavage) is concurrent with a step of purification. For example, a fusion peptide may be passed over an affinity column, the heterologous polypeptide or the purification tag may bind the affinity column and, while bound, a cutting agent may be applied such that the cleavage site is cut and the fusion peptide decomposes.

As is conventional, the designation "$NH_2$" or "N—" refers to the N-terminus of an amino acid sequence and the designation "COOH" or "C—" refers to the C-terminus of an amino acid sequence.

The term "naturally-occurring", "native" or "wild-type" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is wild-type.

A "mutation" as used herein refers to a variation in a nucleotide or amino acid sequence as compared to the wild type sequence. A mutation or "alteration" herein is usually a manufactured nucleic acid change within a coding polynucleotide sequence that results in an alternate but synonymous codon (i.e., the encoded amino acid residue does not change as a result of the mutation). The production and identification of such mutant, synonymous codon optimized, sequences are as further described herein.

The term "control sequence" as used herein refers to polynucleotide sequences which are necessary to effect the expression and processing of coding sequences to which they are ligated. The term "control sequences" is intended to include, at a minimum, all components whose presence is essential for expression and processing, and can also include additional components whose presence is advantageous, for example, leader sequences and fusion partner sequences. A control sequence may be a "Transcription Control Element (TCE)", the nature of which differs depending upon the host organism. A person with ordinary skill in the art will recognize that in prokaryotes, such TCEs generally include promoter, ribosomal binding site, and transcription termination sequences while in eukaryotes, generally, such TCEs include promoters and transcription termination sequences. Control sequences may be regulatable (inducible, for example) or constitutive.

According to the invention any promoter may be used. Promoter usually refers to the nucleotide sequence upstream (5') to the coding sequence and controls the expression of the coding sequence by providing the recognition of the RNA polymerase and other factors which are necessary for the correct transcription. The promoter used according to the invention may comprise a minimal promoter which specify the transcription start site to which regulator elements are attached for expression control.

The term "operably linked" or "operatively linked" as used herein refers to the positioning of components such that they are in a relationship permitting them to function in their intended manner. A person with ordinary skill in the art will recognize that under certain circumstances and depending on the nature of the components (e.g., a cleavage site or purification tag), two or more components "operably linked" together are not necessarily contiguously linked or contiguously associated. A control sequence "operably linked" to a coding sequence is ligated in such a way that expression of the coding sequence is achieved under conditions compatible with the control sequences. If two polynucleotide sequences are said to be operably linked to a control sequence such as a transcription control element (TCE) (or more than one transcription control element), a person with ordinary skill in the art will recognize that a variety of configurations are functional and encompassed. For example, a person with ordinary skill in the art will recognize that at least all the following configurations are encompassed: NH2-the transcription control element-the first polynucleotide sequence-the second polynucleotide sequence-COOH; NH2-the transcription control element-the second polynucleotide sequence-the first polynucleotide sequence-COOH; NH2-the first transcription control element-the first polynucleotide sequence-the second transcription control element-the second polynucleotide sequence-COOH; NH2-the second transcription control element-the second polynucleotide sequence-the first transcription control element-the first polynucleotide sequence-COOH; NH2-the first transcription control element-the second polynucleotide sequence-the second transcription control element-the first polynucleotide sequence-COOH; NH2-the second transcription control element-the first polynucleotide sequence-the first transcription control element-the second polynucleotide sequence-COOH; and combinations thereof. Further, for example, if a mutant triacontanucleotide sequence is said to be operatively linked to a polynucleotide sequence encoding a polypeptide, a nucleic acid sequence encoding a purification tag, and a cleavage site, a person with ordinary skill in the art will recognize that a variety of configurations are functional and encompassed. For example, such a person will recognize that at least the following configurations are encompassed (from the 5' to the 3' end): 5'-(the mutant triacontanucleotide sequence)-(the cleavage site)-(the polynucleotide sequence encoding a polypeptide)-3'; 5'-(the nucleic acid sequence encoding a purification tag)-(the mutant triacontanucleotide sequence)-(the cleavage site)-(the polynucleotide sequence encoding a polypeptide)-3; 5'-(the mutant triacontanucleotide sequence)-(the cleavage site)-(the polynucleotide sequence encoding a polypeptide)-(the nucleic acid sequence encoding a purification tag)-3'; and combinations thereof.

The similarity between two nucleic acid sequences, or two amino acid sequences, is referred to as "sequence identity." Sequence identity is frequently measured in terms of percentage identity (or similarity); the higher the percentage, the more similar the two sequences are. Homologs or orthologs of human polypeptides, and the corresponding cDNA or gene sequence(s), will possess a relatively high degree of sequence identity when aligned using standard methods. This sequence identity will be more significant when the orthologous proteins or genes or cDNAs are derived from species that are more closely related (e.g., human and chimpanzee sequences), compared to species more distantly related (e.g., human and *C. elegans* sequences).

Methods of alignment of sequences for comparison are well known in the art. Various programs and alignment algorithms are described in: Smith & Waterman Adv. Appl. Math. 2: 482, 1981; Needleman & Wunsch J. Mol. Biol. 48: 443, 1970; Pearson & Lipman Proc. Natl. Acad. Sci. USA 85: 2444, 1988; Higgins & Sharp Gene, 73: 237-244, 1988; Higgins & Sharp CABIOS 5: 151-153, 1989; Corpet et al. Nuc. Acids Res. 16, 10881-90, 1988; Huang et al. Computer Appls. in the Biosciences 8:155-65, 1992; and Pearson et al. Meth. Mol. Bio. 24:307-31, 1994. Altschul et al. J. Mol. Biol. 215:403-410, 1990, presents a detailed consideration of sequence alignment methods and homology calculations.

The NCBI Basic Local Alignment Search Tool (BLAST) (Altschul et al. *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. By way of example, for comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment is performed using the Blast 2 sequences function, employing the PAM30 matrix set to default parameters (open gap 9, extension gap 1 penalties).

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The Tm is the temperature (under defined ionic strength and pH) at which 50% of the target sequence remains hybridized to a perfectly matched probe or complementary strand. Conditions for nucleic acid hybridization and calculation of stringencies can be found in Sambrook et al. (In Molecular Cloning: A Laboratory Manual, CSHL, New York, 1989) and Tijssen (Laboratory Techniques in Biochemistry and Molecular Biology—Hybridization with Nucleic Acid Probes Part I, Chapter 2, Elsevier, New York, 1993).

Nucleic acid sequences that do not show a high degree of sequence identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

The phrase "synonymous codon and codon context effects on translation" may b e referred to using the acronym CEOT (codon effects on translation).

The phrase "synonymous codon mutant" (SCM) herein refers to a coding sequence that has been mutagenized so as to comprise one or more synonymous codons as compared to the wild type coding sequence. The phrase "SCM flgM" refers to a flgM coding sequence that has been mutagenized and comprises one or more synonymous codons as a result of that mutagenesis (i.e., "SCM flgM" refers to a mutant flgM coding sequence). As used herein, "synonymous codon mutagenesis/alteration" (SCA) refers to the step of mutating (i.e., altering) a coding sequence such that the resulting mutant/altered sequence comprises one or more synonymous codons as compared to a corresponding control sequence.

Methods of Assaying Translation Speed

The present invention relates to an assay for determining translation speed that takes advantage of the characterization of the regulatory mechanism called transcriptional attenuation in the histidine biosynthetic (his) operon of *Salmonella* (see Chevance et al., PLOS Genetics 10(6):1-14 (2014)). The transcription of the his structural genes is dependent on levels of charged histidyl-tRNA in the cell and independent of mRNA or leader peptide stability. The 5'-region of the his operon has a 16 amino acid open reading frame with seven consecutive His codons. When charged His-tRNA levels are high, attenuation occurs and RNA polymerase ceases transcription of the his operon. If charged His-tRNA is low the ribosome stalls within the stretch of seven His codons and the attenuation mechanism is thwarted so that RNA polymerase continues into the his structural genes in response to limiting His-tRNA. A system was developed to measure the rate of translation through individual codons, pairs of codons, triplets, etc., and measure in vivo how fast the ribosome can translate through different codons for the same amino acid (so-called silent codons or synonymous codons). In this way, an assay was developed for translation speed and determining how one or more synonymous codons effect translation speed.

An exemplary system was produced by replacing the his structural genes with the lac operon as a reporter for His attenuation. With the his attenuation system controlling lac operon transcription, this system may take advantage of color indicator media to provide simple, qualitative color-readouts of attenuation. Based on colony-color phenotypes, the levels of his-lac constructs that are either attenuated or non-attenuated are determined. Using the lac operon reporter system, the His5 position of the leader peptide is substituted with all 63 codons and the effect of individual codons on the degree of ribosomal stalling in the leader peptide region was measured (Id.). Levels of de-attenuation that resulted from the stalling of the ribosome due to the codon change at His5 was measured. Stop cod on s (UAA, UAG and UGA) exhibited the highest levels of de-attenuation while the arginine codons AGA and AGG showed high levels of de-attenuation (Id.). Comparing third positions NNU versus NNC that are read by a single tRNA species, translation of NNU showed a higher level of de-attenuation compared to NNC (Id.). This is consistent with in vitro studies showing that NNG is translated faster than the cognate NNU by a single tRNA species.

The use of this translation speedometer assay for measuring the effects of codon context on translation speed was further demonstrated by measuring the effects of each codon in both 5' and 3' context with the UCA codon. The UCA codon is particularly useful because it is translates by only one essential tRNA species, the SerT tRNA. his-lac expression on Mac-Lac indicator media for all UCA-NNN and NNN-UCA codon pairs placed at His4-His5 in the his operon leader peptide was determined. 22 of the 64 codons exhibited codon context effects. In other words, translation speeds were different for the UCA-NNN and NNN-UCA codon pair for 22 of the 64 codons. The most dramatic context effects were obtained with tyrosine codons. The UCA-UAU and UCA-UAC constructs exhibited levels of de-attenuation comparable to those that were produced by stop codons. However, in the reverse orientation, UAU-UCA and UAC-UCA, de-attenuation is low. The UCA-UAU and UCA-UAC codon pairs are translated at a slow rate whereas the reverse orientations UAU-UCA and UAC-UCA are translated at fast rates. The codon context effect with the CGU codon is also dramatic. Both UCA-CGU and CGU-UCA exhibits a fast translation rate, yet CAU(His)-CGU at the His4-His-5 positions is translated at a very slow rate.

Methods of Modulating Translation Speed

Bacteria comprise a variety of secretion systems with varying structures and functions. Gram-negative bacteria, for example, comprise at least six different secretion systems (Types I-VI) spanning one or both of the outer and inner membranes and playing roles in environmental response, adhesion, or pathogenicity processes (see, e.g., Costa et al., *Secretion systems in Gram-negative bacteria: structural and mechanistic insights*, Nature Reviews, Microbiology 13:343-359 (2015)). For flagella assembly, for example, bacteria may utilize a secretion system (T3SS, e.g.,) by which proteins that are required for flagellum structure and assembly are exported from the cytoplasm, pass the outer membrane, and through the growing flagellar structure.

The *Salmonella enterica* flagellum contains a complex motor structure, known as the hook-basal body (HBB) complex, that is embedded in the cell wall and membranes. The HBB is connected to a long, external filament that extends about 10 microns from the cell surface. The external filament, comprising up to 10,000 FliC subunits, extends from the HBB. Each filament represents about 1% of the total cell protein. The proton motive force powers the rotation of the motor-filament to propel the bacterium through liquid environments and across surfaces. The HBB also contains a type III secretion system that directs the secretion of substrates through a central channel of the structure. Subunits travel to the tip of the growing organelle where they self-assemble into place.

There are over 60 genes in the flagellar regulon, which includes the genes of the chemosensory system. The transcription of these genes is coupled to flagellum assembly as shown in FIG. 1. The flagellar regulon is organized into a transcriptional hierarchy of three promoter classes. The Class 1 operon is often called the master operon and encodes the transcriptional regulators FlhD and FlhC. The FlhD and FlhC proteins form a complex, $FlhD_4C_2$, which directs $\sigma^{70}$ RNA polymerase-dependent transcription from flagellar Class 2 promoters. Genes expressed from Class 2 promoters encode the proteins necessary from the structure and assembly of the HBB complex. In addition to HBB genes, several regulatory proteins are transcribed from Class 2 promoters; prominent among these are the σ28 structural gene, FliA, and the anti-$\sigma^{28}$ gene, FlgM. σ28 and FlgM are regulatory proteins that couple transcription of the flagellar class 3 promoters to completion of the HBB. The $\sigma^{28}$ protein is a flagellar-specific transcription factor that directs RNA polymerase to transcribe from the flagellar class 3 promoters. Class 3 genes include the structural genes of the flagellar filament and genes of the chemosensory signal transduction system that controls the direction of flagellar rotation according to changing concentrations of extracellular ligands.

During HBB assembly, the flagellar type III secretion (T3S) system is specific for rod-hook secretion substrates. Upon HBB completion, the FlhB component of the T3S apparatus undergoes a conformational change and the secretion specificity switches to Late or Filament-type secretion. Prior to HBB completion, FlgM inhibits $\sigma^{28}$-dependent transcription from flagellar Class 3 promoters. FlgM is a late secretion substrate and upon HBB completion and the secretion specificity switch, FlgM is secreted from the cell, releasing σ28 to transcribe from Class 3 promoters.

The FlgM protein comprises a secretion signal at its N-terminus that is not cleaved during the secretion process. Substrate secretion through the T3SS is often facilitated by chaperone-assisted delivery of substrates to the secretion apparatus. In this way, FlgM secretion is greatly enhanced by the binding of the secretion chaperone $\sigma^{28}$ to the C-terminal half of FlgM.

Because FlgM is a small T3S substrate and not part of the final flagellar structure, it can be used as a vehicle to direct secretion of foreign proteins into the periplasm or into the extracellular milieu. The inventors have shown that FlgM polynucleotide sequences operably linked to a heterologous coding sequence may be expressed in various organisms and secreted by the flagellar T3S system (see U.S. PG PUB NO. 2015/0225466, incorporated herein by reference in its entirety). Specifically, a chimeric protein comprising a FlgM peptide fused to a heterologous protein is expressed and secreted through the flagellar T3SS structures and into culture media (see U.S. PG PUB NO. 2015/0225466, incorporated herein by reference in its entirety). The inventors have further shown that expression of a FlgM fusion peptide may be controlled using inducible and/or overexpression control sequences, it may be manipulated by the salt concentration (e.g., NaCl and KCl) within media, and the fusion peptide or its components may be isolated from media using a variety of means (Id.).

The examples herein further demonstrate the use of a T3SS for the modulated production and secretion of chimeric proteins into culture media. In one embodiment, the polypeptide is insulin.

As used herein, the term "insulin" means the active principle of the pancreas that affects the metabolism of carbohydrates in the animal body and which is of value in the treatment of diabetes mellitus. The term includes synthetic and biotechnologically derived products that are the same as, or similar to, naturally occurring insulins in structure, use, and intended effect and are of value in the treatment of diabetes mellitus.

The term "insulin" or "insulin molecule" is a generic term that designates the 51 amino acid heterodimer comprising the A-chain peptide having the amino acid sequence shown in SEQ ID NO: 1 and the B-chain peptide having the amino acid sequence shown in SEQ ID NO: 2, wherein the cysteine residues a positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond. The term "insulin" also includes precursors of insulin molecules.

The term "insulin analog" as used herein includes any heterodimer analog that comprises one or more modification(s) of the native A-chain peptide and/or B-chain peptide. Modifications include but are not limited to substituting an amino acid for the native amino acid at a position selected from A4, A5, A8, A9, A10, A12, A13, A14, A15, A16, A17, A18, A19, A21, B1, B2, B3, B4, B5, B9, B10, B13, B14, B15, B16, B17, B18, B20, B21, B22, B23, B26, B27, B28, B29, and B30; and/or deleting any or all of positions B1-4 and B26-30. Insulin analogs include molecules having one to 10 amino acids at the N or C terminus of the A-chain peptide and/or B-chain peptide. Insulin analogs further include molecules amidated at the C-terminus of the A-chain peptide and/or B-chain peptide. Examples of insulin analogs include but are not limited to the heterodimer analogs disclosed in published international application WO20100080606, WO2009/099763, and WO2010080609, the disclosures of which are incorporated herein by reference. Insulin glargine (Gly(A21), Arg(B31), Arg(B32)-human insulin), insulin lispro (Lys(B28), Pro (B29)-human insulin, insulin glusiline (Lys(B3), Glu(B29)-human insulin), and insulin detemir (Lys-myristic acid (B29)-human insulin) are examples of commercially available insulin analogs.

The term "insulin analogs" further includes heterodimer polypeptide molecules that have little or no detectable activity at the insulin receptor but which have been modified to include one or more amino acid modifications or substitutions to have an activity at the insulin receptor that has at least 1%, 10%, 50%, 75%, or 90% of the activity at the insulin receptor as compared to native insulin. In particular aspects, the insulin analog is a partial agonist that has from 2× to 100× less activity at the insulin receptor as does native insulin. In other aspects, the insulin analog has enhanced activity at the insulin receptor.

Further described herein are expression systems utilizing synonymous codon mutants within a flagellar secretion system gene and methods of modulating heterologous polynucleotide translation when operably appended to such mutants. The synonymous codon mutagenesis of the present invention differs from traditional, codon optimization that relies on the codon usage (bias) of the host cell (organism). Codon usage bias relies on the relative amount that a particular codon is used by a particular organism. The art has long recognized that, between organisms, one synonymous codon for an amino acid is more prevalent (used with higher frequency) as compared to other synonymous codons for that same amino acid (i.e., an organism "prefers" or has a "bias" toward the use of a particular synonymous codon). Divergent organisms may prefer different synonymous codons and therefore have a different codon usage bias.

A table of codon usage frequency in *Escherichia coli* and *Salmonella enterica* is shown below. Therein, a higher usage frequency value corresponds to a greater bias (preference) toward that synonymous codon (available at WorldWideWeb.sci.sdsu.edu/~smaloy/MicrobialGenetics/topics/rev-sup/wobble.html, last visited Nov. 15, 2015). See also The Codon Bias Database (WorldWideWeb.homepages.luc.edu/~cputonti/cbdb/genera/shigella.html) and Hilterbrand, et al. (*CBDB: The codon bias database*, BMC Bioinformatics 13(62):1-7 (2012)).

| Codon preference in *E. coli* and *S. typhimurium* genes.[1] | | | | | | | | | | | |
|---|---|---|---|---|---|---|---|---|---|---|---|
| | | U | | | C | | | A | | | G |
| U | UUU | Phe | 19 | UCU | Ser | 9 | UAU | Tyr | 15 | UGU | Cys | 4 U |
| | UUC | Phe | 17 | UCC | Ser | 10 | UAC | Tyr | 12 | UGC | Cys | 6 C |
| | UUA | Leu | 11 | UCA | Ser | 6 | UAA | STOP | 2 | UGA | STOP | 0.8 A |
| | UUG | Leu | 12 | UCG | Ser | 8 | UAG | STOP | 0.2 | UGG | Trp | 12 G |
| C | CUU | Leu | 10 | CCU | Pro | 7 | CAU | His | 11 | CGU | Arg | 23 U |
| | CUC | Leu | 10 | CCC | Pro | 5 | CAC | His | 10 | CGC | Arg | 23 C |
| | CUA | Leu | 4 | CCA | Pro | 7 | CAA | Gln | 13 | CGA | Arg | 3 A |
| | CUG | Leu | 55 | CCG | Pro | 15 | CAG | Gln | 31 | CGG | Arg | 5 G |
| A | AUU | Ile | 27 | ACU | Thr | 9 | AAU | Asn | 17 | AGU | Ser | 7 U |
| | AUC | Ile | 27 | ACC | Thr | 25 | AAC | Asn | 24 | AGC | Ser | 16 C |
| | AUA | Ile | 4 | ACA | Thr | 6 | AAA | Lys | 36 | AGA | Arg | 2 A |
| | AUG | Met | 2 | ACG | Thr | 15 | AAG | Lys | 12 | AGG | Arg | 1 G |
| G | GUU | Val | 17 | GCU | Ala | 16 | GAU | Asp | 33 | GGU | Gly | 24 U |
| | GUC | Val | 16 | GCC | Ala | 25 | GAC | Asp | 22 | GGC | Gly | 33 C |
| | GUA | Val | 12 | GCA | Ala | 16 | GAA | Glu | 43 | GGA | Gly | 6 A |
| | GUG | Val | 26 | GCG | Ala | 27 | GAG | Glu | 20 | GGG | Gly | 10 G |

[1] The numbers represent the average frequency of codon usage per 1000 codons based upon the DNA sequence of about 450,000 genes in *E. coli* and *S. typhimurium*. Some additional codon frequencies can be found in Miller (1992).

Generally, the presence of a host cell's preferred synonymous codons for, for example, the expression of a heterologous polynucleotide sequence within that host cell results in increased translation efficiency. Traditional codon optimization techniques utilize codon usage bias by mutagenizing a coding sequence such that the host cell's preferred codons are present to increase translation efficiency or absent to decrease translation efficiency.

Synonymous codon mutations in the fliA, fliC and flgM genes of the Salmonella Type III Secretion System have been isolated that either increase or decrease gene expression. For fliA, a synonymous codon 13 (Asp) change from GAU to GAC resulted in a 2-fold increase in $\sigma^{28}$ protein produced (Barker, C. S., et al., *Assembling Flagella in Salmonella Mutant Strains Producing a Type III Export Apparatus without FliO*, J. Bacteriol. 196(23):4001-4011 (2014)). Similarly, for the fliC gene of the Salmonella T3SS, a synonymous codon 13 (Leu) change from UUG to CUG produced ~2- fold more FliC protein, whereas synonymous codon changes at codon 14 (Thr) from ACC to either ACA or ACG produced ~2-fold and ~1.5- fold more FliC protein, respectively (Rosu, V., et al., *Translation Inhibition of the Salmonella fliC Gene by the FliC 5' Untranslated Region, fliC Coding Sequences, and FlgM*, J. Bacteriol. 188(12): 4497-4507 (2006)).

Based on codon usage bias as depicted within the table above, for example, the preference of *Salmonella* for the Asp GAU codon (33) over GAC (22) renders the at least about 2-fold increase in protein production using the GAC codon surprising (Barker et al., supra). Likewise, the preference for the Thr ACC codon (25) over the ACA (6) and ACG (15) codons renders the at least about 2-fold and 1.5-fold increase in protein production using the ACA and ACG codons, respectively, surprising (Rosu et al., supra).

EXAMPLES

Bacterial Strains and Media

The commonly used non-pathogenic strain of *Salmonella enterica* serovar *Typhimurium* LT2 was used for all experiments. LT2 harbors mutations in the ropS and mviA genes that render it avirulent (Yams, *Rates of aminoacyl-tRNA selection at 29 sense codons in vivo*, J. Mol. Biol. 209: 65-77 (1989); Hughes & Roth, *Transitory cis complementation: a method for providing transposition functions to defective transposons*, Genetics 119: 9-12 (1988); Johnston & Roth, *Genetic analysis of the histidine operon control region of Salmonella typhimurium*, J. Mol. Biol. 145: 713-734 (1981)). The mviA gene encodes for the regulator of a two-component system involved in *Salmonella* virulence. The rpoS gene product (stationary-phase sigma transcription factor) is required for the expression of multiple virulence factors. The two mutations within the virulence pathway of *Salmonella* result in attenuation of virulence.

Cells were cultured in Luria-Bertani (LB) medium and, when necessary, supplemented with ampicillin (100 µg/milliliter) or tetracycline (15 µg/milliliter). The generalized transducing phage of *S. Typhimurium* P22 HT105/1 int-201 was used in all transductional crosses (Johnston & Roth, *DNA sequence changes of mutations altering attenuation control of the histidine operon of Salmonella typhimurium*, J. Mol. Biol. 145: 735-756 (1981)).

Strain Construction

Targeted chromosomal mutagenesis was carried out via the tetRA insertion and replacement with the L-Red recombinase system as described in Datsenko and Wanner (*One-step inactivation of chromosomal genes in Escherichia coli K-12 using PCR products*, PNAS 97: 6640-6645 (2000)).

All Primers were synthesized by Integrated DNA Technologies (Coralville, Iowa). All PCR reactions were performed using a proof reading polymerase (Accuprime Pfx, Invitrogen or Phusion, Fermenta). Recombinant products mediated by L-Red were PCR-checked using Taq DNA polymerase and further sequenced.

Screen for Translation-Slowest Codon Pairs

Strains containing slow pair or fast pairs were constructed using by L-Red recombination as described above. After electroporation and plating on anhydrotetracyline plates, the plates were replica printed onto MacConkey-lactose and tetrazolium-lactose indicator plates. White colonies on tetrazolium plates (Lac+) were isolated and sent for DNA sequence analysis. The T-N-N codons were specifically avoided to prevent isolation of stop codons. Tz-Lac screening was used to identify translation-slow and translation-fast codon pairs in the His Leader system.

b-Galactosidase Assays

Thirty microliters of an overnight culture were subcultured into 3 ml of fresh LB medium. Tubes were incubated with shaking at 37° C. until the contents reached a mid-log-phase density of OD 0.4. Cultures were put on ice, spun down, and resuspended in 3 ml of cold-buffered saline. Culture samples of 0.5 ml (diluted if necessary) were added to 0.55 ml of complete Z-buffer (Z-buffer plus 5 ml of 10% sodium dodecyl sulfate and 100 ml of chloroform) (Stanley R. Maloy, EXPERIMENTAL TECHNIQUES IN BACTERIAL GENETICS. (Jones and Bartlett Publishers, Inc. 1990)). The assay was continued as described previously (Id.). For each strain, assays were performed for three independent biological replicates.

Identification of Synonymous Codon Pairs in a Coding Sequence Associated with a Disease or Condition A search for synonymous codon mutations within a polynucleotide sequence (e.g., a coding sequence) associated with a disease or condition is performed using, for example, a database. The synonymous mutations are independent of any additional mutations (including insertions and deletions). Synonymous mutations are parsed based on the 15 base pair sequences flanking either side. The effect a synonymous codon mutation has on the expression of the polynucleotide sequence (expression of an encoded protein, for example) is validated by introducing the synonymous codon mutagenized/altered (SCA) polynucleotide sequence into a host cell and culturing the host cell in conditions sufficient for polynucleotide expression. Any effect is determined by comparison to wild-type polynucleotide expression within a comparable control cell. Resulting protein production is determined by SDS-PAGE and Western blotting.

SDS-PAGE and Western Blotting

Expressed chimeric proteins comprising FlgM (and optionally a poly-Histidine purification tag) or polypeptides expressed from a synonymous codon mutagenized polynucleotide sequence are retrieved from whole-cell lysate or cultural supernatant and subjected to SDS polyacrylamide gel electrophoresis and then analyzed by immunoblotting using polyclonal anti-FlgM antibodies, monoclonal anti-6× His (rabbit) antibodies, or anti-polypeptide antibodies for detection. Antigen-antibody complexes are visualized by chemiluminescent or infrared detection using the LI-COR Odyssey or Bio-Rad ChemiDoc imaging system. For chemiluminescent development, secondary goat anti-rabbit antibodies (Bio-Rad) conjugated with horseradish peroxidase (HRP) and an ECL detection kit (Amersham Biosciences) are used. For infrared detection, secondary anti-rabbit IRDye690 (LI-COR) are used. Densiometric measurements of protein bands are performed using ImageJ 1.45 s for Mac OS X (Abramoff et al., *Image processing with ImageJ*, Biophotonics Int. 11:36-42(2004)).

Recombinant Expression and Purification of Protein Fusions

Cells expressing optimized fusion proteins are picked from a fresh single colony and grown in 10 ml LB overnight. The overnight cultures are diluted 1:100 into 1 liter of fresh medium in a baffled flask and grown in a shaking incubator at 200 rpm for 6-12 hours. If appropriate, expression is induced after the first 2 hours by the addition of 0.2% arabinose or Na-Salicylate. Cells are pelleted by centrifugation (7,000 rpm), and the supernatant containing the recombinant polypeptide of interest is passed through a 0.22-μm polyethersulfone filter (Corning, N.Y.), a low-protein-binding membrane for removal of residual bacteria. For further purification, a gravity flow column (Bio-Rad) packed with 3 g Ni-IDA resin (Protino Ni-IDA; Machery-Nagel) is used, and affinity-tagged proteins are eluted under native conditions at pH 7.5 with a buffer containing 250 mM imidazole.

Secretion Assay

Overnight cultures are diluted 1:100 in LB and grown for 2 h at 37° C. before inducing the expression of the respective FlgM fusions by adding 0.2% L-arabinose. Cells are kept at 37° C. for an additional 4-12 hours, while the fusion proteins are expressed. Afterwards, the optical density at 600 nm ($OD_{600}$) is determined for all strains.

Two-milliliter aliquots of the resulting cell culture are centrifuged for 10 min at 4° C. and 7,000 rpm to obtain, for each aliquot, a pellet and supernatant. The supernatant is filtered through a low-protein-binding filter with a 0.2-μm pore size (Acrodisk syringe filter; Pall Life Sciences) to remove the remaining cells. Alternatively, aliquots are centrifuged twice at maximum speed to remove residual cells. Secreted proteins in the filtered or twice-centrifuged supernatant are precipitated by the addition of TCA (10% final concentration). The supernatant samples are resuspended in 24, SDS sample buffer (100 mM Tris [pH 6.8], 4% SDS, 10% glycerol, 2% B-mercaptoethanol, 25 mM EDTA, 0.04% bromophenol blue) and adjusted to 20 $OD_{600}$ units/μ. The cellular pellet fraction is suspended in 2% SDS sample buffer, whose volume is adjusted to yield 20 $OD_{600}$ units/μL.

Example 1: Effects of Synonymous Codon Mutants on Translation

An allele of the SerT tRNA that is defective in translating the UCA for amino acid Ser7 of the flagellar anti-$\sigma^{28}$ gene, flgM was isolated (Chevance, F. F., et al., *J Bacteriol* 188:297-304 (2006)). Despite there being many genes with UCA codons for serine in the *Salmonella* flagellar system, the serT tRNA mutant allele only effected flgM translation. Without being bound by theory, it is believed that the effect of the serT mutant allele on translation of the UCA (Ser7) codon of flgM is a codon-context effect.

Transcription from a $\sigma^{28}$-dependent promoter is inhibited by FlgM. Using the bacterial luciferase operon (lux) as a reporter, the anti-$\sigma^{28}$ activity of FlgM was measured. When FlgM activity is high, $\sigma^{28}$-dependent transcription of $P_{motA}$-lux is low. Synonymous mutations were introduced adjacent to position Ser7 and the effects of flanking synonymous mutations on flgM mRNA translation was determined.

All 16 combinations of synonymous changes of the Thr6 and Pro8 codons flanking the UCA Ser7 codon of flgM were made. The FlgM inhibition of $\sigma^{28}$-dependent $P_{motA}$-lux transcription was measured. Results were as shown at FIG. 2.

The synonymous changes at Thr6 to ACU, ACA or ACG produce an about 11- to 13-fold increase in FlgM inhibitory activity. The synonymous Pro8 codon change CCU to CCG results in an about 20-fold reduction in FlgM inhibitory activity. The combination of a ACC to ACU change at Thr6 with a CCU to CCG change at Pro8 results in an about 34-fold increase in FlgM inhibitory activity. These results demonstrate that the efficiency of codon translation is influenced by up to two adjacent codons (see FIG. 2).

Example 2: Modulation of Polynucleotide Translation Using Synonymous Mutagenesis of FlgM Starting with a flgM sequence comprising the CCU to CCG change at Pro8, the region of the flgM gene that encodes amino acids 2 through 25 was modified using doped oligonucleotide mutagenesis designed so that, on average, each oligonucleotide had a synonymous codon change for amino acids 2 through 25. Results were as shown in FIG. 3.

Only synonymous changes in the two codons preceding Pro8 and the Leu9 codon following Pro8 CCG resulted in restoration to wild-type FlgM inhibitory activity. These results demonstrate that efficiency of translation of a specific codon is dependent on the flanking two codons.

Synonymous variations coding for amino acids Thr6-Ser7-Pro8-Leu9 of FlgM result in an about ~2-fold range in FlgM protein levels. However, since FlgM is a regulatory protein that inhibits $\sigma^{28}$-dependent fliC transcription, the about 2-fold range in FlgM protein levels produces more than an about 1000-fold range in fliC transcription activity. For example, a synonymous codon change at codon 8 of flgM from CCU to CCG (encoding Proline) resulted in an about 2-fold lower FlgM protein level. The about 2-fold reduction in FlgM protein levels resulted in an about 20-fold increase in transcription of the σ28-dependent fliC promoter.

Example 3: Modulation of Heterologous Polynucleotide Translation Using Synonymous Mutagenesis of FlgM The first ten codons of lacZ were replaced with the first ten codons of flgM, and the flgM sequence was mutated to comprise a CCU to CCG synonymous codon change at Pro8 (codon number 8, in the 5' to 3' direction, of flgM that encodes proline). Consistent with the results above, expression of the heterologous lacZ sequence under the control of the context-codon-optimized flgM sequence resulted in reduced β-galactosidase activity. β-galactosidase activity was reduced about 210 to 150 units.

These results demonstrate that synonymous changes in one or more of Thr6-Ser7-Pro8-Leu9 of FlgM effect heterologous protein production (here LacZ) levels when a polynucleotide sequence encoding that polypeptide (here lacz) is operably linked to the context-codon-optimized FlgM sequence (SCM FlgM) and expressed and secreted through a bacterial secretion system (here an engineered T3SS).

Exemplary polypeptides that may be recombinantly produced using a secretion system of the present invention are listed in Table 1 below.

TABLE 1

| Protein | Exemplary sequence information |
|---------|-------------------------------|
| Insulin (human) | A chain: GIVEQCCTSICSLYQLENYCN (SEQ ID NO: 17) <br> B chain: FVNQHLCGSHLVEALYLVCGE RGFFYTPKT (SEQ ID NO: 18) |

TABLE 1-continued

| Protein | Exemplary sequence information |
|---------|-------------------------------|
| Insulin glargine (human) | A chain: GIVEQCCTSICSLYQLENYCG (SEQ ID NO: 19) <br> B chain: FVNQHLCGSHLVEALYLVCGE RGFFYTPKTRR (SEQ ID NO: 20) |
| Insulin pre-proinsulin (human) | See UniProtKB Accession No. P01308 and GenBank Accession No. CAA49913 (Chekhranova et al., Mol. Biol. 26(3): 596-600 (1992)): MALWMRLLPLLALLALTA7GPDPAAAFVNQHLCG SHLVEALYLVCGERGFFYIPKTRREAEDLQVGQV ELGGGPGAGSLQPLALEGSLQKRGIVEQCCTSIC SLYQLENYCN (SEQ ID NO: 21) <br> An exemplary mRNA sequence is available at GenBank Accession No. X70508 (Chekhranova et al., Mol. Biol. 26(3): 596-600 (1992)). |
| Insulin lisopro | A chain: GIVEQCCTSICSLYQLENYCN (SEQ ID NO: 22) <br> B chain: FVNQHLCGSHLVEALYLVCGE RGFFYTKPT (SEQ ID NO: 23) |
| MaSp1 (Major Ampullate Spidroin 1; spider silk protein) (including, e.g., MaSp1A or MaSp1B from *Nephila* spiders) | See Gaines and Marcotte, Insect Mol. Biol. 17(5): 465-474 (2008); U.S. Pat. No. 8,642,734 (incorporated herein by reference in its entirety); U.S. Pat. No. 7,521,228 (incorporated herein by reference in its entirety); US PG PUB NO. 2014/0093965 (incorporated herein by reference in its entirety). |
| MaSp2 (Major Ampullate Spidroin 2; spider silk protein) | U.S. Pat. No. 8,642,734 (incorporated herein by reference in its entirety); U.S. Pat. No. 7,521,228 (incorporated herein by reference in its entirety); US PG PUB NO. 2014/0093965 (incorporated herein by reference in its entirety) incorporated herein by reference in. |

Example 4: Modulation of Heterologous Protein Production Using a T3SS

A nucleic acid molecule comprising a full-length, wild type FlgM polynucleotide sequence operably linked to a human insulin glargine nucleic acid sequence, a poly-histidine nucleotide sequence, an enterokinase cleavage site, and a ParaBAD promoter was introduced into and expressed within a *Salmonella enterica* serovar *Typhimurium* cell. The *Salmonella* cell was modified within several T3S genes as previously described by the inventors (see U.S. PG PUB NO. 2015/0225466, incorporated herein by reference in its entirety) and specifically comprised: ParaBAD1::flgM-His6-ETK-insulin glargine ΔflgMN7753 ΔflgKL7770 PflhDC7793 fliA*5225 ΔfliB-T7771 fljB$_{enx}$ vh2 (referred to as Strain TS1). A FlgM::Insulin chimeric protein was secreted by the cell and detected via Western blot using anti-6xHis antibodies. Results are shown in FIG. 4.

Example 5: Modulation of Heterologous Protein Production Using a T3SS and Synonymous Mutagenesis Secretion of human insulin from an engineered *Salmonella* T3SS may be further optimized by introducing and expressing within a *Salmonella* cell a FlgM nucleotide sequence (either a wild type or a synonymous codon mutated FlgM sequence) that is operably linked to a poly-hisitidine purification tag nucleic acid sequence, a cleavage site (e.g., an enterokinase cleave site), and polynucleotide sequences encoding the A and B chains of human insulin wherein the human insulin B chain sequence comprises a synonymous codon mutation. For example, the two adjacent arginine residues within the human insulin B chain may be context codon optimized to increase insulin expression and secretion through the T3SS. In particular, wild type adjacent arginine codons CGC and CGG (in the 5' to 3' direction) may be mutated to CGU and CGU; CGU and CGC; CGC and CGU; CGC and CGC; or CGG and CGC. An exemplary construct comprising nucleic acid sequences encoding, in the N-terminal to C-terminal direction, a poly-histidine purification tag, a cleavage site, and human insulin is provided by SEQ ID NO: 16. The sequence provided by SEQ ID NO: 16 may be appended to a FlgM sequence as described elsewhere herein and by the inventors at U.S. PG PUB NO. 2015/0225466 (incorporated herein by reference in its entirety). It is expected that the resulting pair of synonymous codon optimized arginine codons will cause increased human insulin expression and secretion. A chimeric protein comprising FlgM, a poly-histidine purification tag, a cleavage site, and insulin may be detected and purified as described above. The insulin protein may be isolated from the chimeric protein as described above.

TABLE 2

| Sequence Identifier | Description of sequence | Sequence (written in the 5' to 3' direction or N-terminus to C-terminus direction) |
|---|---|---|
| 1 | The first ten amino acid residues of wild-type FlgM protein (corresponds to the first 10 residues of SEQ ID NO: 3). | MSIDRTSPLK |
| 2 | The first ten codons (i.e., 30 nucleotides) of the wild-type FlgM mRNA sequence. | ATGAGCATTGACCGTACCTCACCTTTGAAA |
| 3 | The full-length, 97 residue wild-type FlgM amino acid sequence (Gillen and Hughes, J. Bacteriology 173(20): 6453-6459 (1991); publically available at, e.g., GenBank Accession No. AAA27075 and UniProtKB Accession No. P26477). The first ten residues (i.e., SEQ ID NO: 1) underlined. | MSIDRTSPLKPVSTVQTRETSDTPVQKTRQE<br>KTSAATSASVTLSDAQAKLMQPGVSDINMER<br>VEALKTAIRNGELKMDTGKIADSLIREAQSY<br>LQSK |
| 4 | Wild type FlgM gene sequence (Gillen and Hughes, J. Bacteriology 173(20): 6453-6459 (1991); publically available at, e.g., GenBank Accession No. M74222). Coding region (i.e., SEQ ID NO: 5) underlned. First ten codons thereof (i.e., SEQ ID NO: 2) in bold. | AATATTCTTATTAACCTATAATTGTGTAAAGATT<br>TTGTCGCGGCTGCCGATGAGATATTCAACCATGA<br>TG<br>GTAGCTGGCCGCTACAACGTAACCCTCGATGAGG<br>ATAAATAAATGAGCATTGACCGTACCTCACCTTT<br>GA<br>AACCCGTTAGCACTGTCCAGACGCGCGAAACCAG<br>CGACACGCCGGTACAAAAAACGCGTCAGGAAAAA<br>AC<br>GTCCGCCGCGACGAGCGCCAGCGTAACGTTAAGC<br>GACGCGCAAGCGAAGCTCATGCAGCCAGGCGTCA<br>GC<br>GACATTAATATGGAACGCGTCGAAGCATTAAAAA<br>CGGCTATCCGTAACGGTGAGTTAAAAATGGATAC<br>GG<br>GAAAAATAGCAGACTCGCTCATTCGCGAGGCGCA<br>GAGCTACTTACAGAGTAAATAAGCGTATGACTCG<br>TT<br>TGTCAGAAATACTTGACCAGATGACCACCGTCCT<br>GAATGACCTGAAGACGGTGATGGACGCCGAGCAA<br>CA<br>ACAGCTTTCCGTAGGCCAGATTAACGGCAGCCAG<br>CTACAGCGTATTACAGAAGAAAAAAGCTCGTTGC<br>TG<br>GCGACGCTGGATTATCTGGAACAACAGCGCCGTC<br>TGGAGCAGAATGC |
| 5 | Full-length, wild type flgM coding region and stop codon (corresponds to nucleotides 113 to 406 of SEQ ID NO: 4, stop codon underlined). | ATGAGCATTGACCGTACCTCACCTTTGAAAC<br>CCGTTAGCACTGTCCAGACGCGCGAAACCAG<br>CGACACGCCGGTACAAAAAACGCGTCAGGAA<br>AAAACGTCCGCCGCGACGAGCGCCAGCGTAA<br>CGTTAAGCGACGCGCAAGCGAAGCTCATGCA<br>GCCAGGCGTCAGCGACATTAATATGGAACGC<br>GTCGAAGCATTAAAAACGGCTATCCGTAACG<br>GTGAGTTAAAAATGGATACGGGAAAAATAGC |

TABLE 2-continued

| Sequence Identifier | Description of sequence | Sequence (written in the 5' to 3' direction or N-terminus to C-terminus direction) |
| --- | --- | --- |
| | | AGACTCGCTCATTCGCGAGGCGCAGAGCTAC TTACAGAGTAAA<u>TAA</u> |
| 6 | Full-length, wild type flgM mRNA (first ten codons (i.e., mRNA sequence corresponding to SEQ ID NO: 2) in bold, stop codon underlined). | AUGAGCAUUGACCGUACCUCACCUUUGAAAC CCGUUAGCACUGUCCAGACGCGCGAAACCAG CGACACGCCGGUACAAAAAACGCGUCAGGAA AAAACGUCCGCCGCGACGAGCGCCAGCGUAA CGUUAAGCGACGCGCAAGCGAAGCUCAUGCA GCCAGGCGUCAGCGACAUUAAUAUGGAACGC GUCGAAGCAUUAAAAACGGCUAUCCGUAACG GUGAGUUAAAAAUGGAUACGGGAAAAAUAGC AGACUCGCUCAUUCGCGAGGCGCAGAGCUAC UUACAGAGUAAA<u>UAA</u> |
| 7 | AGCSer2AGT synonymous codon mutant triacontanucleotide flgM sequence. Mutation underlined. | ATG<u>AGT</u>ATTGACCGTACCTCACCTTTGAAA |
| 8 | ACCThr6ACA synonymous codon mutant triacontanucleotide flgM sequence. Mutation underlined. | ATGAGCATTGACCGT<u>ACA</u>TCACCTTTGAAA |
| 9 | ACCThr6ACG synonymous codon mutant triacontanucleotide flgM sequence. Mutation underlined. | ATGAGCATTGACCGT<u>ACG</u>TCACCTTTGAAA |
| 10 | ACCThr6ACT synonymous codon mutant triacontanucleotide flgM sequence. Mutation underlined. | ATGAGCATTGACCGT<u>ACT</u>TCACCTTTGAAA |
| 11 | TCASer7TCG synonymous codon mutant triacontanucleotide flgM sequence. Mutation underlined. | ATGAGCATTGACCGTACC<u>TCG</u>CCTTTGAAA |
| 12 | TCASer7TCC synonymous codon mutant triacontanucleotide flgM sequence. Mutation underlined. | ATGAGCATTGACCGTACC<u>TCC</u>CCTTTGAAA |
| 13 | TCASer7TCT synonymous codon mutant triacontanucleotide flgM sequence. Mutation underlined. | ATGAGCATTGACCGTACC<u>TCT</u>CCTTTGAAA |
| 14 | CCTPro8CCG synonymous codon mutant triacontanucleotide flgM sequence. Mutation underlined. | ATGAGCATTGACCGTACCTCA<u>CCG</u>TTGAAA |
| 15 | TTGLeu9TTA synonymous codon mutant triacontanucleotide flgM sequence. Mutation underlined. | ATGAGCATTGACCGTACCTCACCT<u>TTA</u>AAA |
| 16 | Human insulin glargine construct comprising a poly-histidine purification tag sequence (in bold), a cleavage site (in underline), and pre-pro insulin sequence (B chain in bold and underline, A chain in bold and double underline). | ATG CAT CAT CAT CAT CAT CAT <u>GGT GGC CGC</u> TTT GTG AAC CAA CAC CTG TGC GGC TCA CAC CTG GTG GAA GCT CTC TAC CTA GTG TGC GGG GAA CGA GGC TTC TTC TAC ACA CCC AAG ACC <u>CGC CGG</u> GAG GCA GAG GAC CTG CAG GTG GGG CAG GTG GAG CTG GGC GGG GGC CCT GGT GCA GGC AGC CTG CAG CCC TTG GCC CTG GAG GGG TCT CTG CAG GCG CGT <u>GGC ATT GTG GAA CAA TGC TGT ACC AGC</u> <u>ATC TGC TCC CTC TAC CAG CTG GAG AAC TAC TGC GGC TAG</u> |

It is to be appreciated that the Detailed Description section, and not the Summary and Abstract sections, is intended to be used to interpret the claims. The Summary and Abstract sections sets forth one or more, but not all, exemplary embodiments of the present invention as contemplated by the inventor(s), and thus, are not intended to limit the present invention and the appended claims in any way. All of the patents, patent applications and references cited herein are incorporated by reference in their entirety.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

What is claimed is:

1. A recombinant nucleic acid molecule comprising a mutant triacontanucleotide sequence having at least ten codons, wherein at least one of the sixth, seventh, eighth, ninth and tenth codons, in the 5' to 3' direction, are synonymous codons, and wherein the mutant triacontanucleotide sequence is selected from SEQ ID NOs: 8-15.

2. The recombinant molecule of claim 1, wherein the mutant triacontanucleotide sequence is operably linked to a heterologous polynucleotide sequence that encodes a polypeptide of interest.

3. The recombinant molecule of claim 2, wherein the polypeptide of interest is insulin.

4. A vector comprising the recombinant molecule of claim 1.

5. An isolated host cell comprising the recombinant molecule of claim 1.

6. A vector comprising the recombinant molecule of claim 2.

7. An isolated host cell comprising the recombinant molecule of claim 2.

8. A method of modulating protein production within a host cell, comprising culturing a host cell under conditions sufficient for protein expression, wherein the recombinant molecule of claim 4 has been stably introduced into the host cell.

9. A method of increasing the translation speed of a polynucleotide sequence, comprising providing to a host cell a polynucleotide sequence that encodes a protein and is operably linked to a wild type triacontanucleotide sequence comprising ten codons and encoding SEQ ID NO:1, and mutating the triacontanucleotide sequence so that the mutant triacontanucleotide sequence is selected from SEQ ID NOs: 8-15, and culturing the host cell under conditions to express the polynucleotide sequence.

10. A method for increasing specific cellular productivity of a polypeptide of interest in a host cell comprising: (a) providing a polynucleotide sequence that encodes the polypeptide of interest and is operably linked to a wild type triacontanucleotide sequence comprising ten codons and encoding SEQ ID NO:1, (b) mutating the triacontanucleotide sequence so that the mutant triacontanucleotide sequence is selected from SEQ ID NOs: 8-15; (c) introducing the polynucleotide sequence into the host cell; (d) incubating the cell under conditions wherein the introduced polynucleotide is expressed; and (e) isolating the polypeptide of interest.

* * * * *

SEQUENCE LISTING

<160> NUMBER OF SEQ ID NOS: 23

<210> SEQ ID NO 1
<211> LENGTH: 10
<212> TYPE: PRT
<213> ORGANISM: Salmonella typhimurium

<400> SEQUENCE: 1

Met Ser Ile Asp Arg Thr Ser Pro Leu Lys
1               5                   10

<210> SEQ ID NO 2
<211> LENGTH: 30
<212> TYPE: DNA
<213> ORGANISM: Salmonella typhimurium

<400> SEQUENCE: 2
atgagcattg accgtacctc acctttgaaa                                        30

<210> SEQ ID NO 3
<211> LENGTH: 97
<212> TYPE: PRT
<213> ORGANISM: Salmonella typhimurium

<400> SEQUENCE: 3

Met Ser Ile Asp Arg Thr Ser Pro Leu Lys Pro Val Ser Thr Val Gln
1               5                   10                  15

Thr Arg Glu Thr Ser Asp Thr Pro Val Gln Lys Thr Arg Gln Glu Lys
            20                  25                  30

Thr Ser Ala Ala Thr Ser Ala Ser Val Thr Leu Ser Asp Ala Gln Ala
        35                  40                  45

Lys Leu Met Gln Pro Gly Val Ser Asp Ile Asn Met Glu Arg Val Glu
    50                  55                  60

Ala Leu Lys Thr Ala Ile Arg Asn Gly Glu Leu Lys Met Asp Thr Gly
65                  70                  75                  80

Lys Ile Ala Asp Ser Leu Ile Arg Glu Ala Gln Ser Tyr Leu Gln Ser
                85                  90                  95

Lys

<210> SEQ ID NO 4
<211> LENGTH: 607
<212> TYPE: DNA
<213> ORGANISM: Salmonella typhimurium

<400> SEQUENCE: 4
aatattctta ttaacctata attgtgtaaa gattttgtcg cggctgccga tgagatattc      60
aaccatgatg gtagctggcc gctacaacgt aaccctcgat gaggataaat aaatgagcat     120
tgaccgtacc tcacctttga aacccgttag cactgtccag acgcgcgaaa ccagcgacac     180
gccggtacaa aaaacgcgtc aggaaaaaac gtccgccgcg acgagcgcca gcgtaacgtt     240

```
aagcgacgcg caagcgaagc tcatgcagcc aggcgtcagc gacattaata tggaacgcgt    300
cgaagcatta aaacggcta tccgtaacgg tgagttaaaa atggatacgg gaaaaatagc    360
agactcgctc attcgcgagg cgcagagcta cttacagagt aaataagcgt atgactcgtt    420
tgtcagaaat acttgaccag atgaccaccg tcctgaatga cctgaagacg gtgatggacg    480
ccgagcaaca acagctttcc gtaggccaga ttaacggcag ccagctacag cgtattacag    540
aagaaaaaag ctcgttgctg gcgacgctgg attatctgga caacagcgc cgtctggagc     600 agaatgc                                                              607
```

```
<210> SEQ ID NO 5
<211> LENGTH: 294
<212> TYPE: DNA
<213> ORGANISM: Salmonella typhimurium

<400> SEQUENCE: 5
```

```
atgagcattg accgtacctc acctttgaaa cccgttagca ctgtccagac gcgcgaaacc     60
agcgacacgc cggtacaaaa aacgcgtcag gaaaaaacgt ccgccgcgac gagcgccagc    120
gtaacgttaa gcgacgcgca agcgaagctc atgcagccag cgtcagcga cattaatatg    180 gaacgcgtcg aagcattaaa aacggctatc cgtaacggtg agttaaaaat ggatacggga    240
aaaatagcag actcgctcat tcgcgaggcg cagagctact tacagagtaa ataa          294
```

```
<210> SEQ ID NO 6
<211> LENGTH: 294
<212> TYPE: RNA
<213> ORGANISM: Salmonella typhimurium

<400> SEQUENCE: 6
```

```
augagcauug accguaccuc accuuugaaa cccguuagca cuguccagac gcgcgaaacc     60
agcgacacgc cgguacaaaa aacgcgucag gaaaaaacgu ccgccgcgac gagcgccagc    120
guaacguuaa gcgacgcgca agcgaagcuc augcagccag cgucagcga cauuauaug    180 gaacgcgucg aagcauuaaa aacggcuauc cguaacggug aguuaaaaau ggauacggga    240
aaaauagcag acucgcucau ucgcgaggcg cagagcuacu uacagaguaa auaa          294
```

```
<210> SEQ ID NO 7
<211> LENGTH: 30
<212> TYPE: DNA
<213> ORGANISM: Artificial Sequence
<220> FEATURE:
<223> OTHER INFORMATION: AGCSer2AGT synonymous codon mutant
      triacontanucleotide  flgM sequence

<400> SEQUENCE: 7
```

```
atgagtattg accgtacctc acctttgaaa                                      30
```

```
<210> SEQ ID NO 8
<211> LENGTH: 30
<212> TYPE: DNA
<213> ORGANISM: Artificial Sequence
<220> FEATURE:
<223> OTHER INFORMATION: ACCThr6ACA synonymous codon mutant
      triacontanucleotide  flgM sequence

<400> SEQUENCE: 8
```

```
atgagcattg accgtacatc acctttgaaa                                      30
```

```
<210> SEQ ID NO 9
<211> LENGTH: 30
```

```
<212> TYPE: DNA
<213> ORGANISM: Artificial Sequence
<220> FEATURE:
<223> OTHER INFORMATION: ACCThr6ACG synonymous codon mutant
      triacontanucleotide  flgM sequence

<400> SEQUENCE: 9
atgagcattg accgtacgtc acctttgaaa                                           30

<210> SEQ ID NO 10
<211> LENGTH: 30
<212> TYPE: DNA
<213> ORGANISM: Artificial Sequence
<220> FEATURE:
<223> OTHER INFORMATION: ACCThr6ACT synonymous codon mutant
      triacontanucleotide

<400> SEQUENCE: 10
atgagcattg accgtacttc acctttgaaa                                           30

<210> SEQ ID NO 11
<211> LENGTH: 30
<212> TYPE: DNA
<213> ORGANISM: Artificial Sequence
<220> FEATURE:
<223> OTHER INFORMATION: TCASer7TCG synonymous codon mutant
      triacontanucleotide  flgM sequence

<400> SEQUENCE: 11
atgagcattg accgtacctc gcctttgaaa                                           30

<210> SEQ ID NO 12
<211> LENGTH: 30
<212> TYPE: DNA
<213> ORGANISM: Artificial Sequence
<220> FEATURE:
<223> OTHER INFORMATION: TCASer7TCC synonymous codon mutant
      triacontanucleotide  flgM sequence

<400> SEQUENCE: 12
atgagcattg accgtacctc ccctttgaaa                                           30

<210> SEQ ID NO 13
<211> LENGTH: 30
<212> TYPE: DNA
<213> ORGANISM: Artificial Sequence
<220> FEATURE:
<223> OTHER INFORMATION: TCASer7TCT synonymous codon mutant
      triacontanucleotide  flgM sequence

<400> SEQUENCE: 13
atgagcattg accgtacctc tcctttgaaa                                           30

<210> SEQ ID NO 14
<211> LENGTH: 30
<212> TYPE: DNA
<213> ORGANISM: Artificial Sequence
<220> FEATURE:
<223> OTHER INFORMATION: CCTPro8CCG synonymous codon mutant
      triacontanucleotide  flgM sequence

<400> SEQUENCE: 14
atgagcattg accgtacctc accgttgaaa                                           30

<210> SEQ ID NO 15
<211> LENGTH: 30
<212> TYPE: DNA
```

```
<213> ORGANISM: Artificial Sequence
<220> FEATURE:
<223> OTHER INFORMATION: TTGLeu9TTA synonymous codon mutant
      triacontanucleotide   flgM sequence

<400> SEQUENCE: 15
atgagcattg accgtaccct cacctttaaaa                                      30

<210> SEQ ID NO 16
<211> LENGTH: 291
<212> TYPE: DNA
<213> ORGANISM: Artificial Sequence
<220> FEATURE:
<223> OTHER INFORMATION: Human insulin glargine construct

<400> SEQUENCE: 16
atgcatcatc atcatcatca tggtggccgc tttgtgaacc aacacctgtg cggctcacac    60
ctggtggaag ctctctacct agtgtgcggg gaacgaggct tcttctacac acccaagacc   120
cgccgggagg cagaggacct gcaggtgggg caggtggagc tgggcggggg ccctggtgca   180
ggcagcctgc agcccttggc cctggagggg tctctgcagg cgcgtggcat tgtggaacaa   240
tgctgtacca gcatctgctc cctctaccag ctggagaact actgcggcta g            291

<210> SEQ ID NO 17
<211> LENGTH: 21
<212> TYPE: PRT
<213> ORGANISM: Homo sapiens

<400> SEQUENCE: 17

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 18
<211> LENGTH: 30
<212> TYPE: PRT
<213> ORGANISM: Homo sapiens

<400> SEQUENCE: 18

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 19
<211> LENGTH: 21
<212> TYPE: PRT
<213> ORGANISM: Homo sapiens

<400> SEQUENCE: 19

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 20
<211> LENGTH: 32
<212> TYPE: PRT
<213> ORGANISM: Homo sapiens

<400> SEQUENCE: 20
```

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30
```

<210> SEQ ID NO 21
<211> LENGTH: 110
<212> TYPE: PRT
<213> ORGANISM: Homo sapiens

<400> SEQUENCE: 21

```
Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110
```

<210> SEQ ID NO 22
<211> LENGTH: 21
<212> TYPE: PRT
<213> ORGANISM: Artificial Sequence
<220> FEATURE:
<223> OTHER INFORMATION: Insulin lisopro A chain

<400> SEQUENCE: 22

```
Gly Ile Val Glu Gln Cys Cys Thr Ser Ile Cys Ser Leu Tyr Gln Leu
1               5                   10                  15

Glu Asn Tyr Cys Asn
            20
```

<210> SEQ ID NO 23
<211> LENGTH: 30
<212> TYPE: PRT
<213> ORGANISM: Artificial Sequence
<220> FEATURE:
<223> OTHER INFORMATION: Insulin lisopro B chain

<400> SEQUENCE: 23

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30
```